United States Patent [19]

Miyazaki et al.

[11] Patent Number: 5,527,763
[45] Date of Patent: Jun. 18, 1996

[54] PYRIMIDINE OR TRIAZINE DERIVATIVES AND HERBICIDES

[75] Inventors: Masahiro Miyazaki; Masafumi Matsuzawa; Takumi Yoshimura; Kuniaki Shimizu, all of Iwataegun; Shigehiko Tachikawa, Shizuoka, all of Japan

[73] Assignees: Kumiai Chemical Industry Co., Ltd.; Ihara Chemical Industry Co., Ltd., both of Tokyo, Japan

[21] Appl. No.: 107,716

[22] PCT Filed: Dec. 24, 1992

[86] PCT No.: PCT/JP92/01690

§ 371 Date: Dec. 8, 1993

§ 102(e) Date: Dec. 8, 1993

[87] PCT Pub. No.: WO93/13078

PCT Pub. Date: Jul. 8, 1993

[30] Foreign Application Priority Data

Dec. 24, 1991 [JP] Japan ................. 3-355688

[51] Int. Cl.$^6$ .............. A01N 43/54; C07D 401/12; C07D 239/32
[52] U.S. Cl. .............. 504/242; 504/192; 504/239; 504/243; 544/300; 544/301; 544/302; 544/310; 544/311; 544/312; 544/315; 544/316; 544/317; 544/318; 544/319; 544/320; 544/324; 544/328; 544/331; 544/332; 544/333
[58] Field of Search .............. 504/192, 239, 504/242, 243; 544/296, 300, 301, 320, 302, 310, 311, 312, 315, 316, 317, 318, 319, 324, 328, 331, 332, 333

[56] References Cited

U.S. PATENT DOCUMENTS

| | | | |
|---|---|---|---|
| 4,818,270 | 4/1989 | Grabiak et al. | 544/296 |
| 5,015,285 | 5/1991 | Rheinheimer et al. | 504/243 |
| 5,149,357 | 9/1992 | Dixson et al. | 504/243 |
| 5,262,385 | 11/1993 | Goh et al. | 504/239 |

FOREIGN PATENT DOCUMENTS

| | | |
|---|---|---|
| 0171286 | 2/1986 | European Pat. Off. |
| 0360163 | 3/1990 | European Pat. Off. |
| 52-122384 | 10/1977 | Japan |
| 55-149283 | 11/1980 | Japan |
| 58-162587 | 9/1983 | Japan |
| 61-83167 | 4/1986 | Japan |
| 256469 | 8/1987 | Japan |
| 63-146876 | 6/1988 | Japan |
| 1-249773 | 10/1989 | Japan |
| 3-284676 | 3/1990 | Japan |

OTHER PUBLICATIONS

CA 111:232863, 1989.
CA 101:230261, 1984.
CA 88:104310, 1977.
CA 89:215138, 1978.
CA 73:14605, 1970.

*Primary Examiner*—Yogendra N. Gupta
*Attorney, Agent, or Firm*—Oblon, Spivak, McClelland, Maier & Neustadt

[57] ABSTRACT

A herbicide containing a pyrimidine or triazine derivative of the formula (I):

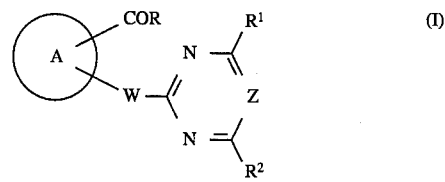

[wherein A is a furan ring, a pyrimidine ring, a 1,2,4-triazine ring or the like which may suitably be substituted, R is a hydroxyl group or a lower alkoxy group, each of $R^1$ and $R^2$ which may be the same or different, is a halogen atom, a lower alkyl group or a lower alkoxy group, W is an oxygen atom or a sulfur atom, and Z is nitrogen or a methine group] and its salt, as an active ingredient, is presented. The pyrimidine or triazine derivative of the present invention has excellent herbicidal effects against noxious weeds in paddy fields, upland fields and non-agricultural fields.

3 Claims, No Drawings

PYRIMIDINE OR TRIAZINE DERIVATIVES AND HERBICIDES

TECHNICAL FIELD

This application is a 371 of PCT/JP 92/01690, filed on Dec. 14, 1992.

The present invention relates to herbicides which contain pyrimidine or triazine derivatives and their salts as active ingredients and which can be applied to paddy fields, upland fields and non-agricultural fields.

BACKGROUND ART

It has been already disclosed in Japanese Unexamined Patent Publication No. 121973/1990 that the following compounds have herbicidal activities:

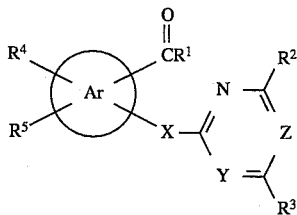

However, the herbicidal effects off the compounds disclosed in this publication are not necessarily adequate. The present inventors have conducted extensive researches on pyrimidine or triazine compounds with an aim to develop further improved compounds and as a result, have found that pyrimidine or triazine derivatives of the present invention having a heterocyclic ring introduced exhibit excellent herbicidal effects not only against annual weeds but also against perennial weeds, and they are highly safe to crop plants. The present invention has been accomplished on the basis of this discovery.

DISCLOSURE OF THE INVENTION

The present invention provides a pyrimidine or triazine derivative of the formula (I):

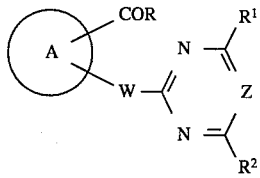

wherein A is a heterocyclic ring of the formula:

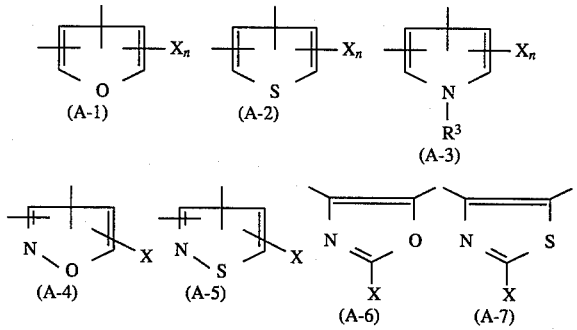

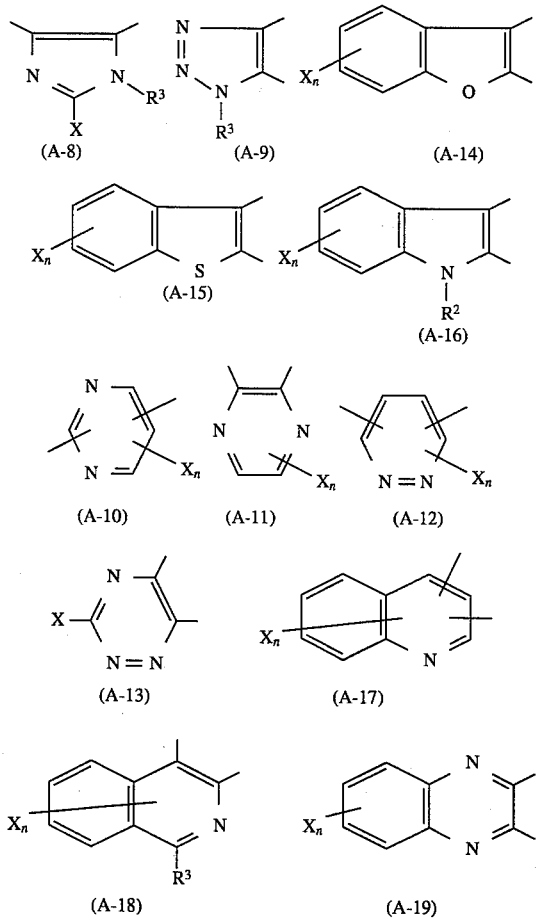

R is a hydrogen atom, a hydroxyl group, an imidazolyl group, a $C_1$–$C_6$ alkoxy group, a $C_3$–$C_6$ alkenyloxy group, a $C_3$–$C_6$ alkynyloxy group, a $C_1$–$C_6$ alkylthio group, a $C_3$–$C_7$ cycloalkoxy group, a benzyloxy group, a substituted benzyloxy group, a benzylthio group, a substituted benzylthio group, a $C_3$–$C_6$ cycloalkylthio group, a $C_1$–$C_4$ alkoxy $C_1$–$C_4$ alkoxy group, a furyloxy group, a tetrahydrofuryloxy group, a phenoxy group, a substituted phenoxy group, a $C_2$–$C_4$ aralkyloxy group, a $C_1$–$C_4$ alkylthio $C_1$–$C_4$ alkoxy group, a cyano $C_1$–$C_4$ alkoxy group, a $C_1$–$C_4$ alkoxycarbonyl $C_1$–$C_4$ alkoxy group, an N,N-di $C_1$–$C_3$ alkylamino $C_1$–$C_3$ alkoxy group, an N,N-di $C_1$–$C_3$ alkylamino $C_1$–$C_3$ alkylthio group, a $C_3$–$C_9$ linear or cyclic alkylidene aminoxy group, a $C_1$–$C_4$ alkylsulfonylamino group, a phenylsulfonylamino group, a substituted phenylsulfonylamino group, a trimethylsilylethoxy group, a group of the formula —$NR^4R^5$ (wherein each of $R^4$ and $R^5$ which may be the same or different, is a hydrogen atom, a hydroxyl group, a $C_1$–$C_6$ alkyl group, a $C_1$–$C_6$ alkoxy group, a $C_3$–$C_6$ alkenyl group, a phenyl group, a substituted phenyl group, a $C_3$–$C_6$ cycloalkyl group, a $C_1$–$C_3$ alkoxy $C_1$–$C_3$ alkyl group, a $C_1$–$C_3$ acyl group, a $C_3$–$C_6$ alkynyl group, a $C_3$–$C_5$ alkenyloxy group, a $C_3$–$C_5$ alkynyloxy group, a benzyloxy group, a substituted benzyloxy group, a $C_1$–$C_4$ alkoxycarbonyl $C_1$–$C_3$ alkyl group, a $C_1$–$C_4$ alkoxycarbonyl $C_1$–$C_3$ alkoxy group, an amino group, a dimethylamino group, a cyano group, a $C_1$–$C_4$ alkylsulfonyl group, a phenylsulfonyl group, a substituted phenylsulfonyl group, an acetylamino group or an anilino group, or $R^4$ and $R^5$ may together form a ring which may contain a hetero atom), each of $R^1$ and $R^2$ which may be the same or different, is a hydrogen atom (provided that a case where $R^1$ and $R^2$ are the same, is excluded), a halogen atom, a $C_1$–$C_6$ alkyl group, a $C_1$–$C_6$ haloalkyl group, a $C_1$–$C_6$ alkoxy group, a $C_1$–$C_6$ haloalkoxy group, a $C_1$–$C_6$ alkylthio group, a phenoxy group, a substituted phenoxy group, a $C_1$–$C_3$ alkoxy $C_1$–$C_3$ alkyl group, a $C_3$–$C_6$ cycloalkyl group, a $C_2$–$C_5$ alkenyl group, a $C_3$–$C_5$ alkenyloxy group, a $C_2$–$C_4$ alkynyl group, a $C_3$–$C_5$ alkynyloxy group, a $C_1$–$C_3$ alkylthio $C_1$–$C_3$ alkyl group, a group of the formula —$NR^6R^7$ (wherein each of $R^6$ and $R^7$ which may be the same or different, is a hydrogen atom, a hydroxyl group, a $C_1$–$C_4$ alkyl group, a $C_1$–$C_4$ alkoxy group, a $C_2$–$C_4$ alkenyl group, a $C_2$–$C_4$ alkynyl group, a $C_3$–$C_5$ alkenyloxy group or a $C_3$–$C_5$ alkynyloxy group, or $R^6$ and $R^7$ may together form a ring which may contain a hetero atom), $R^3$ is a hydrogen atom, a halogen atom, a $C_1$–$C_6$ alkyl group, a phenyl group, a substituted phenyl group, a benzyl group, a substituted benzyl group, a benzoyl group, a substituted benzoyl group, a $C_1$–$C_3$ acyl group, $C_1$–$C_6$ alkylsulfonyl group, a phenylsulfonyl group or a substituted phenylsulfonyl group, X is a hydrogen atom, a $C_1$–$C_6$ alkyl group, a $C_1$–$C_6$ haloalkyl group, a $C_1$–$C_6$ alkoxy group, a $C_1$–$C_6$ haloalkoxy group, a $C_3$–$C_6$ alkenyl group, a phenyl group, a substituted phenyl group, a benzyl group, a substituted benzyl group, a phenoxy group, a substituted phenoxy group, a benzyloxy group, a substituted benzyloxy group, a $C_1$–$C_3$ acyl group, a naphthyl group, a benzoyl group, a substituted benzoyl group, a halogen atom, a nitro group, a group of the formula —$NR^8R^9$ (wherein each of $R^8$ and $R^9$ which may be the same or different, is a hydrogen atom, a $C_1$–$C_{12}$ alkyl group, a $C_3$–$C_6$ alkenyl group, a $C_3$–$C_6$ alkynyl group, a phenyl group, a substituted phenyl group, a naphthyl group, a $C_1$–$C_3$ acyl group, a benzoyl group or a substituted benzoyl group, or $R^8$ and $R^9$ may together form a ring which may contain a hetero atom), a $C_1$–$C_6$ alkylthio group, a $C_1$–$C_6$ alkylthio $C_1$–$C_3$ alkyl group, a phenylthio group, a substituted phenylthio group, a $C_1$–$C_6$ alkoxycarbonyl group, a carboxyl group, a cyano group, a carbamoyl group, a N—$C_1$–$C_6$ alkylcarbamoyl group, a $C_1$–$C_6$ alkylsulfonyl group, a phenylsulfonyl group, a substituted phenylsulfonyl group, a $C_1$–$C_6$ alkoxy $C_1$–$C_6$ alkyl group, a $C_1$–$C_6$ alkoxy $C_1$–$C_6$ alkoxy group, a $C_1$–$C_6$ alkylthio $C_1$–$C_6$ alkyl group, a $C_1$–$C_6$ alkoxy $C_1$–$C_6$ alkylthio group, a $C_1$–$C_6$ alkylthio $C_1$–$C_6$ alkoxy group, an allylthio group, a $C_1$–$C_6$ alkylsulfinyl group, a furyl group, a thienyl group, a pyridyl group, a pyrimidinyloxy group which may be substituted, a pyrimidinylthio group which may be substituted, a substituted triazinyloxy group, a substituted triazinylthio group, W is an oxygen atom, a sulfur atom or a group of the formula —$NR^{10}$ (wherein $R^{10}$ is a hydrogen atom, a $C_1$–$C_3$ alkyl group, a $C_2$–$C_5$ alkenyl group, a $C_2$–$C_4$ alkynyl group, a $C_1$–$C_3$ alkoxy $C_1$–$C_3$ alkyl group, a $C_1$–$C_3$ alkylsulfonyl group, a phenylsulfonyl group, a substituted phenylsulfonyl group, a $C_1$–$C_3$ acyl group, a benzoyl group or a substituted benzoyl group), Z is a nitrogen atom or a methine group, and n is an integer of from 1 to 5; and its salt; and a herbicide containing such a compound as an active ingredient.

Here, for R, the alkoxy group may, for example, be a methoxy group, an ethoxy group, an isopropoxy group, a propoxy group or a butoxy group, the alkenyloxy group may, for example, be an allyloxy group, the alkynyloxy group may, for example, be a propargyloxy group, the alkylthio group may, for example, be an ethylthio group or a propylthio group, the cycloalkoxy group may, for example, be a cyclopentyloxy group or a cyclohexyl group, the substituted benzyloxy group may, for example, be a benzyloxy group substituted by a chlorine atom, a methyl group or a methoxy group, the substituted benzylthio group may, for example, be a chlorine atom-substituted benzyloxy group, the cycloalkylthio group may, for example, be a cyclopentylthio group, the alkoxyalkoxy group may, for example, be a methoxymethoxy group, the substituted phenoxy group may, for example, be a phenoxy group substituted by a chlorine atom or a methyl group, the aralkyloxy group may, for example, be a phenethyloxy group, the alkylthioalkoxy group may, for example, be a methylthiomethoxy group, the cyanoalkoxy group may, for example, be a cyanomethoxy group, the alkoxycarbonylalkoxy group may, for example, be a methoxycarbonylmethoxy group or an ethoxycarbonylmethoxy group, the N,N-dialkylaminoalkoxy group may, for example, be an N,N-dimethylaminoethoxy group, the N,N-dialkylaminoalkylthio group may, for example, be an N,N-dimethylaminoethylthio group, the linear or cyclic alkylidene aminoxy group may, for example, be an isopropylideneaminoxy group, a 3-pentylideneaminoxy group, a 4-heptylideneaminoxy group, a cyclohexylideneaminoxy group, a cycloheptylideneaminoxy group or a 4-tetrahydropyranylideneaminoxy group, the alkylsulfonylamino group may, for example, be a methylsulfonylamino group or an ethylsulfonylamino group, and the substituted phenylsulfonylamino group may, for example, be a phenylsulfonylamino group substituted by e.g. a chlorine atom, a methyl group, a nitro group or a methoxycarbonyl group.

For $R^4$ or $R^5$ in the formula —$NR^4R^5$, the alkyl group may, for example, be a methyl group, the alkoxy group may, for example, be a methoxy group or an ethoxy group, the substituted phenyl group may, for example, be a phenyl group substituted by e.g. a chlorine atom or a methyl group, the cycloalkyl group may, for example, be a cyclohexyl group, the alkoxyalkyl group may, for example, be a methoxymethyl group or a methoxyethyl group, the acyl group may, for example, be an acetyl group, the alkynyl group may, for example, be a propargyl group, the alkenyloxy group may, for example, be an allyloxy group, the alkynyloxy group may, for example, be a propargyloxy group, the substituted benzyloxy group may, for example, be a chloro-substituted benzyloxy group, the alkoxycarbonylalkyl group may, for example, be a methoxycarbonylmethyl group, the alkoxycarbonylalkoxy group may, for example, be a methoxycarbonylmethoxy group, an ethoxycarbonylmethoxy group or a methoxycarbonylethoxy group, the alkylsulfonyl group may, for example, be a methylsulfonyl group or an ethylsulfonyl group, the alkylsulfonyl group may, for example, be a methylsulfonyl group or an ethylsulfonyl group, the substituted phenylsulfonyl group may, for example, be a phenylsulfonyl group substituted by e.g. a chlorine atom, a methoxycarbonyl group, a methyl group or a nitro group, and the ring which may contain a hetero atom, formed by $R^4$ or $R^5$, may, for example, be a piperidino group, a morpholino group or a pyrrolidino group.

For $R^1$ or $R^2$, the halogen atom may, for example, be a chlorine atom, the alkyl group may, for example, be a methyl group, the haloalkyl group may, for example, be a trifluoromethyl group, the alkoxy group may, for example, be a methoxy group, the haloalkoxy group may, for example, be a difluoromethoxy group, the alkylthio group may, for example, be a methylthio group, the cycloalkyl group may, for example, be a cyclopropyl group, the alkenyloxy group may, for example, be an allyloxy group, the alkynyl group may, for example, be a 1-propynyl group, the alkynyloxy group may, for example, be a 2-propionyloxy group, and the alkylthioalkyl group may, for example, be a methylthiomethyl group. The alkyl group for $R^6$ or $R^7$ of the formula —$NR^6R^7$ may, for example be a methyl group.

For $R^3$, the halogen atom may, for example, be a chlorine atom, the alkyl group may, for example, be a methyl group, the substituted phenyl group may, for example, be a phenyl group substituted by e.g. a chlorine atom or a methyl group, and the substituted benzyl group may, for example, be a benzyl group substituted by e.g. a chlorine atom or a methyl group.

For X, the alkyl group may, for example, be a methyl group, an isopropyl group or a t-butyl group, the haloalkyl group may, for example, be a perfluoroethyl group, the alkoxy group may, for example, be an ethoxy group or an isobutyloxy group, the alkenyl group may, for example, be a 1-propenyl group, the substituted phenyl group may, for example, be a phenyl group substituted by e.g. a chlorine atom, a methyl group or a trifluoromethyl group, the halogen atom may, for example, be a chlorine atom or a fluorine atom, the alkylthio group may, for example, be a methylthio group, the alkylthioalkyl group may, for example, be a methylthiomethyl group, the alkoxycarbonyl group may, for example, be an ethoxycarbonyl group, the alkylsulfonyl group may, for example, be a methylsulfonyl group, the pyridyl group may, for example, be a 3- or 4-pyridyl group, the pyrimidinyloxy group which may be substituted, may, for example, be a (4,6-dimethoxypyrimidin-2-yl)oxy group, and the pyrimidinylthio group which may be substituted, may, for example, be a (4,6-dimethoxypyrimidin-2-yl)thio group. For $R^8$ or $R^9$ in the formula $—NR^8R^9$, the alkyl group may, for example, be a methyl group, an ethyl group or an isopropyl group, the substituted phenyl group may, for example, be a methyl-substituted phenyl group, and the substituted benzoyl group may, for example, be a chlorine atom-substituted benzoyl group.

For $R^{10}$ in the formula $—NR^{10}$ for W, the alkyl group may, for example, be a methyl group, the alkenyl group may, for example, be an allyl group, the alkoxyalkyl group may, for example, be a methoxymethyl group, the alkylsulfonyl group may, for example, be a methylsulfonyl group, and the acyl group may, for example, be a formyl group or an acetyl group.

Compounds of the present invention can be produced, for example, in accordance with the following processes A to H.

Process A

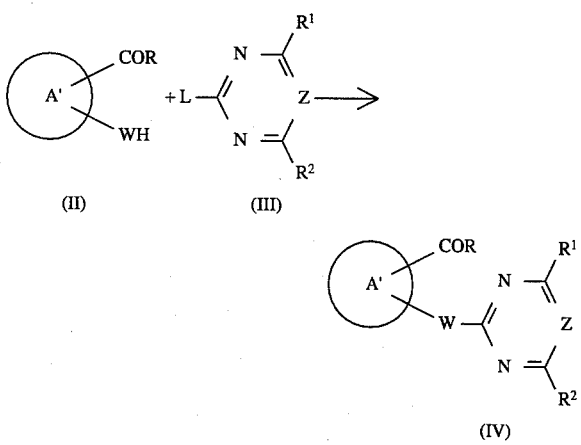

(wherein $A^1$ is a heterocyclic ring of the formula:

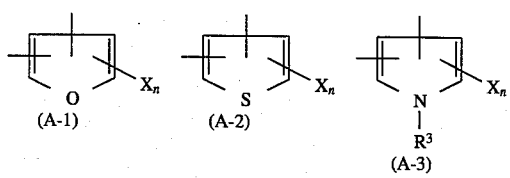

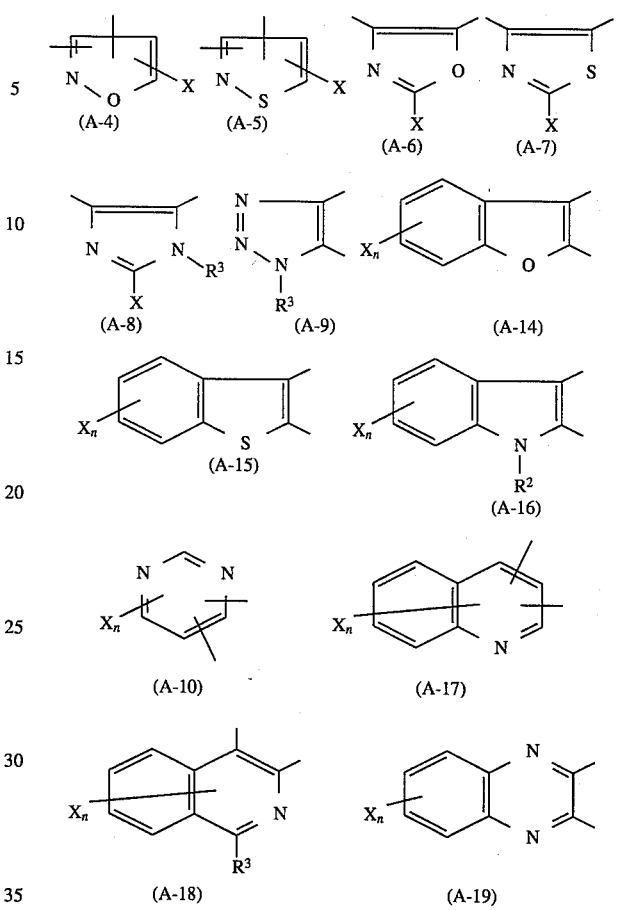

L is a halogen atom, an alkylsulfonyl group, a benzylsulfonyl group, a substituted benzylsulfonyl group, an alkylsulfonate group or a haloalkylsulfonate group, and W, X, Z, n, R, $R^1$, $R^2$ and $R^3$ are as defined above.)

A compound of the formula (IV) can be produced by reacting a compound of the formula (II) with a compound of the formula (III) in a suitable solvent in the presence of an at least equimolar amount of a base at a temperature within a range of from room temperature to the boiling point of the solvent for from 0.5 to 24 hours. As the base, an alkali metal such as metal lithium, metal sodium or metal potassium, an organic lithium reagent such as n-butyl lithium or lithium diisopropylamine, an alkali metal hydride or an alkaline earth metal hydride such as sodium hydride, potassium hydride or calcium hydride, an alkali metal alkoxide such as potassium t-butoxide, an alkali metal carbonate such as sodium carbonate or potassium carbonate, or an alkali metal hydroxide such as sodium hydroxide or potassium hydroxide, may be used. As the solvent, a hydrocarbon solvent such as hexane, benzene, toluene or xylene, a halogenated hydrocarbon solvent such as dichloromethane or chloroform, an ether solvent such as diethyl ether, tetrahydrofuran or 1,4-dioxane, an ester solvent such as methyl acetate or ethyl acetate, a ketone solvent such as acetone or methyl ethyl ketone, an aprotic polar solvent such as N,N-dimethylformamide, N,N-dimethylacetamide or dimethylsulfoxide, or other solvent such as acetonitrile, may be used.

Process B

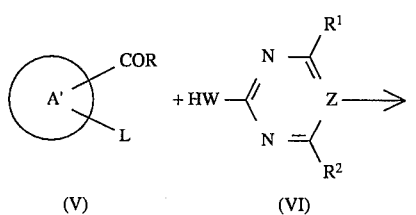

(V)   (VI)

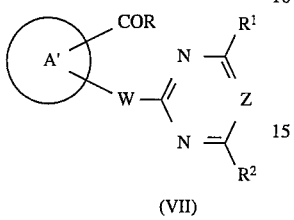

(VII)

(wherein $A^2$ is a heterocyclic ring of the formula:

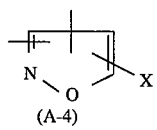 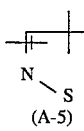 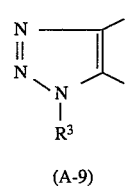
(A-4)   (A-5)   (A-9)

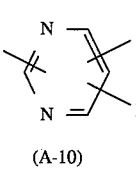 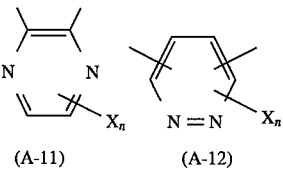
(A-10)  (A-11)  (A-12)

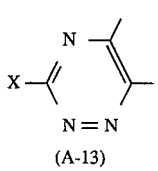 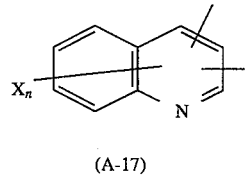
(A-13)  (A-17)

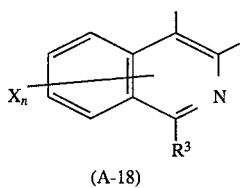 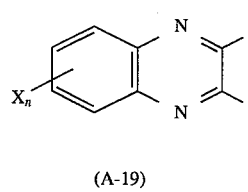
(A-18)  (A-19)

L, W, X, Z, N, n, R, $R^1$, $R^2$ and $R^3$ are as defined above.)

A compound of the formula (VII) can be produced by reacting a compound of the formula (V) with a compound of the formula (VI) in a suitable solvent in the presence of an at least equimolar amount of a base at a temperature within a range of from room temperature to the boiling point of the solvent for from 0.5 to 24 hours. The base and the solvent to be used, may be the same as those described for Process A.

Process C

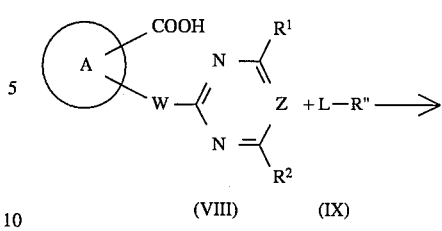

(VIII)   (IX)

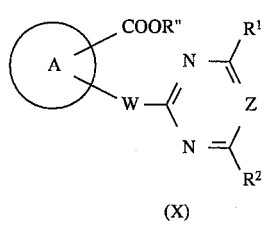

(X)

(wherein $R^{11}$ is a $C_1$–$C_6$ alkyl group, a $C_3$–$C_7$ cycloalkyl group, a benzyl group, a substituted benzyl group, a $C_1$–$C_4$ alkoxy group $C_1$–$C_4$ alkyl group, a tetrahydrofuryl group, a $C_2$–$C_4$ aralkyl group, a $C_1$–$C_4$ alkylthio $C_1$–$C_4$ alkyl group, a cyano $C_1$–$C_4$ alkyl group, a $C_1$–$C_4$ alkoxycarbonyl $C_1$–$C_4$ alkyl group, a N,N-di $C_1$–$C_3$ alkylamino $C_1$–$C_3$ alkyl group, and A, L, $R^1$, $R^2$, W and Z are as defined above.)

A compound of the formula (X) can be produced by reacting a compound of the formula (VIII) with a compound of the formula (IX) in a solvent in the presence of a base at a reaction temperature of from –10° to 200° C. for from 0.1 to 30 hours. Here, as the base, an organic or inorganic base such as potassium carbonate, sodium hydrogencarbonate, sodium hydride, triethylamine, pyridine or 4-dimethylaminopyridine, may be used. Further, as the solvent, acetone, acetonitrile, tetrahydrofuran, N,N-dimethylacetamide, dimethylsulfoxide, benzene, toluene, chlorobenzene, dichloromethane or chloroform may, for example, be used.

Process D

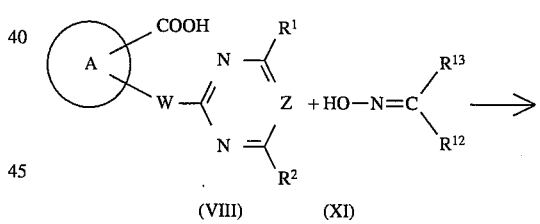

(VIII)   (XI)

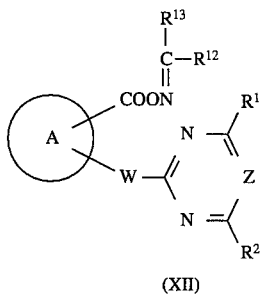

(XII)

(wherein each of $R^{12}$ and $R^{13}$ which may be the same or different, is a $C_1$–$C_4$ alkyl group, or they may form a ring which may contain a hetero atom, and A, W, Z, $R^1$ and $R^2$ are as defined above.)

A compound of the formula (XII) can be produced by reacting a compound of the formula (VIII) with a compound of the formula (XI) in a solvent in the presence of a base and a phosphoric acid dichloride such as dimethylamide phosphoryl dichloride or phenylphosphoro dichloride at a reaction temperature of from 10° to 100° C. for from 1 to 10 hours. Here, as the base, an organic tertiary amine such as pyridine or triethylamine, may, for example, be used. Further, as the solvent, N,N-dimethylformamide, N,N-dimethylacetamide or dimethylsulfoxide may, for example, be used.

Process E

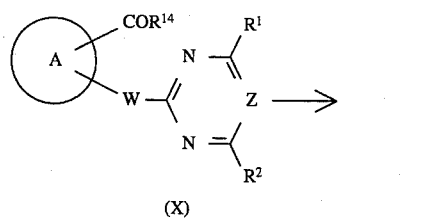

(X)

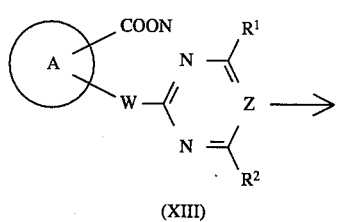

(XIII)

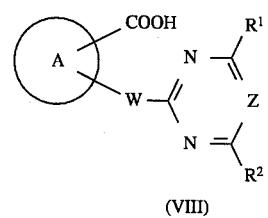

(VIII)

(wherein $R^{14}$ is a $C_1$–$C_6$ alkoxy group, a $C_3$–$C_6$ alkenyloxy group, a $C_3$–$C_6$ alkynyloxy group, a $C_1$–$C_6$ alkylthio group, a $C_3$–$C_7$ cycloalkoxy group, a benzyloxy group, a substituted benzyloxy group, a benzylthio group, a substituted benzylthio group, a $C_3$–$C_6$ cycloalkylthio group, a $C_1$–$C_4$ alkoxy $C_1$–$C_4$ alkoxy group, a furyloxy group, a tetrahydrofuryloxy group, a phenoxy group, a substituted phenoxy group, a $C_2$–$C_4$ aralkyloxy group, a $C_1$–$C_4$ alkylthio $C_1$–$C_4$ alkoxy group, a cyano $C_1$–$C_4$ alkoxy group, a $C_1$–$C_4$ alkoxycarbonyl $C_1$–$C_4$ alkoxy group, a N,N-di $C_1$–$C_3$ alkylamino $C_1$–$C_3$ alkoxy group, a N,N-di $C_1$–$C_3$ alkylamino $C_1$–$C_3$ alkylthio group, a C3-$C_9$ linear or cyclic alkylidene aminoxy group, or a trimethylsilylethoxy group, A, $R^1$, $R^2$, Z and W are as defined above, and M is a monovalent cation.)

A compound of the formula (XIII) can be produced by reacting a compound of the formula (X) in a mixture system of water and a solvent in the presence of a base at a reaction temperature of from 0° to 120° for from 1 to 24 hours. Then, a compound of the formula (VIII) can be obtained by acidifying the compound of the formula (XIII) to pH 3 to 4 by e.g. hydrochloric acid in accordance with a conventional method. Here, as the base, an inorganic base such as sodium hydroxide, potassium hydroxide, sodium carbonate or potassium carbonate may, for example, be used. Further, as the solvent, acetone, acetonitrile, methanol, ethanol, dioxane, tetrahydrofuran, dimethoxyethane, N,N-dimethylformamide, N,N,-dimethylacetamide or dimethylsulfoxide may, for example, be used. In a case where $R^{12}$ in the formula (X) is a benzyl group or a substituted benzyl group, a compound of the formula (VIII) can be obtained by a hydrogenating reaction under an ordinary pressure using e.g. palladium-carbon as a catalyst.

Process F

An organic or inorganic salt of a compound of the formula (XIII) can be produced by reacting a compound of the formula (VIII) with a base in a solvent such as water, an alcohol, acetonitrile, acetone, an ether, N,N-dimethylformamide or dimethylsulfoxide at a reaction temperature of from 0° to 100° C. for from 0.2 to 10 hours. Here, as the base, an alkali metal or an alkaline earth metal hydroxide such as sodium hydroxide, potassium hydroxide or calcium hydroxide, a carbonate such as sodium carbonate, potassium carbonate or calcium carbonate, ammonia, or a primary, secondary or tertiary amine such as ethylamine, dimethylamine, isopropylamine, diisopropylamine, diethanolamine or triethylamine, may be used.

Process G

A compound of the formula (VIII) and an equimolar amount of an aqueous sodium hydroxide solution are reacted at room temperature, then a metal halide such as magnesium chloride, copper chloride, calcium chloride, iron chloride, zinc chloride or manganese chloride and a sulfate such as magnesium sulfate, copper sulfate, calcium sulfate, iron sulfate, zinc sulfate or manganese sulfate are added, and the mixture is reacted in a solvent such as water or an alcohol at a temperature of from −10° C. to 200° C. for from one minute to 20 hours, whereby an inorganic salt of a compound of the formula (XIII) can be produced.

Process H

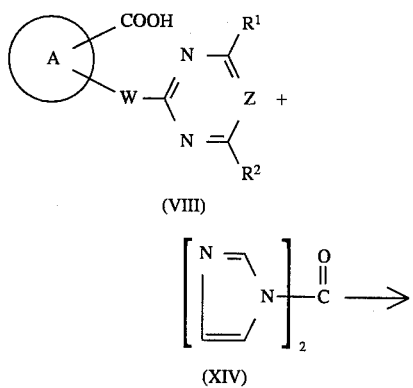

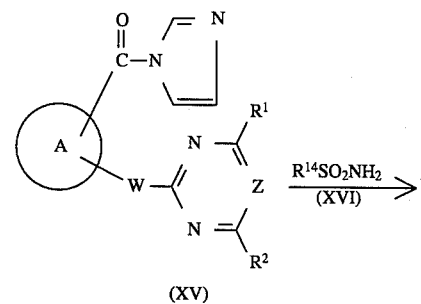

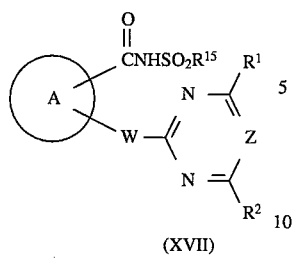

(XVII)

(wherein $R^{15}$ is a $C_1$–$C_4$ alkyl group, a phenyl group or a substituted phenyl group, and $R^1$, $R^2$, W, Z and A are as defined above.)

A compound of the formula (XV) can be produced by reacting a compound of the formula (VIII) with a compound of the formula (XIV) in a solvent at a reaction temperature of from −10° to 100° C. for form 1 to 10 hours. As the solvent, ethyl ether, tetrahydrofuran, dioxane, benzene or toluene may, for example, be used. Then, a compound of the formula (XVII) can be produced by reacting a compound of the formula (XV) with a compound of the formula (XVI) in a solvent in the presence of a base at a reaction temperature of from −20° to 150° C. for from 0.5 to 20 hours. Here, as the base, sodium hydride, metal sodium, potassium t-butoxide, butyl lithium, potassium carbonate or sodium carbonate may, for example, be used. Further, as the solvent, acetone, acetonitrile, tetrahydrofuran, N,N-dimethylformamide, N,N-dimethylacetamide, dimethylsulfoxide, benzene or toluene may, for example, be used.

Now, the processes for producing the compounds of the present invention, methods for preparation of formulations and methods for application will be specifically described with reference to Examples.

BEST MODE FOR CARRYING OUT THE INVENTION

EXAMPLE 1 (Process A)

Preparation of ethyl 1-chloro-4-(4,6-dimethoxypyrimidin-2-yloxy)isoquinoline-3-carboxylate (Compound No. 754)

40 ml of N,N-dimethylformamide was added to 1.8 g (7.1 mmol) of ethyl 1-chloro-4-hydroxyisoquinoline-3-carboxylate, 1.4 g (8.6 mmol) of 4,6-dimethoxy-2-fluoropyrimidine and 1.2 g (8.6 mmol) of potassium carbonate, and the mixture was heated and stirred at from 80° to 100° C. for 3 hours. After cooling, the reaction solution was poured into water and washed with ethyl acetate. The aqueous layer was adjusted to pH 3 to 4 with a 10% HCl solution and extracted with ethyl acetate. The organic layer was washed with water and a saturated sodium chloride aqueous solution and then dried over anhydrous sodium sulfate. Then, the solvent was distilled off under reduced pressure, and the residue was purified by column chromatography to obtain 0.6 g (yield: 21.4%) of the desired product. Refractive index: 1.5811.

EXAMPLE 2 (Process A)

Preparation of methyl 3-(4,6-dimethoxypyrimidin-2-yloxy)benzofuran-2-carboxylate (Compound No. 674)

100 ml of N,N-dimethylsulfoxide was added to 5.0 g (26.0 mmol) of methyl 3-hydroxybenzofuran-2-carboxylate, 4.6 g (28.9 mmol) of 4,6-dimethoxy-2-fluoropyrimidine and (43.4 mmol) of potassium carbonate, and the mixture was heated and stirred at from 80° to 100° C. for 30 minutes. After cooling, the reaction solution was poured into water, extracted with ethyl acetate, washed with water and a saturated sodium chloride aqueous solution and then dried over anhydrous sodium sulfate. Then, the solvent was distilled off under reduced pressure, and the residue was purified by column chromatography to obtain 3.6 g (yield: 41.9%) of the desired product. Melting Point: 135°–138° C.

EXAMPLE 3 (Process A)

Preparation of ethyl 4-(4,6-dimethoxypyrimidin-2-yloxy)-2-methylthiomethylthiophene-3-carboxylate (Compound No. 170)

50 ml of N,N-dimethylformamide was added to 3.5 g (15.1 mmol) of ethyl 4-hydroxy-2-methylthiomethylthiophene-3-carboxylate, 3.3 g (15.1 mmol) of 4,6-dimethoxy-2-methylsulfonylpyrimidine and 2.1 g (15.2 mmol) of potassium carbonate, and the mixture was heated and stirred at from 90° to 100° C. for 2 hours. After cooling, the reaction solution was poured into water, extracted with ethyl acetate, washed with water and a saturated sodium chloride aqueous solution, and then dried over anhydrous sodium sulfate. Then, the solvent was distilled off under reduced pressure, and the residue was purified by column chromatography to obtain 2.8 g (yield: 50.0%) of the desired product.

EXAMPLE 4 (Process B)

Preparation of methyl 3-(4,6-dimethoxypyrimidin-2-yloxy)pyrazine-2-carboxylate (Compound No. 622)

150 ml of N,N-dimethylformamide was added to 3.5 g (2.03 mmol) of methyl 3-chloropyrazine-2-carboxylate, 3.6 g (2.31 mmol) of 4,6-dimethoxy-2-hydroxypyrimidine and 4.2 g (3.04 mmol) of potassium carbonate, and the mixture was heated and stirred at 100° C. for 25 hours. After cooling, the reaction solution was poured into water, extracted with ethyl acetate, washed with water and a saturated sodium chloride aqueous solution, and then dried over anhydrous sodium sulfate. Then, the solvent was distilled off under reduced pressure, and the residue was purified by column chromatography to obtain 0.5 g (yield: 7.0%) of the desired product. Melting point: 88°–93° C.

EXAMPLE 5 (Process B)

Preparation of ethyl 3-(4,6-dimethoxypyrimidin-2-yloxy)quinoxaline-2-carboxylate (Compound No. 762)

100 ml of N,N-dimethylformamide was added to 2.3 g (9.72 mmol) of ethyl 3-chloroquinoxaline-2-carboxylate, 2.0 g (12.8 mmol) of 4,6-dimethoxy-2-hydroxypyrimidine and 1.8 g (13.0 mmol) of potassium carbonate, and the mixture was heated and stirred at 100° C. for 23 hours. After cooling, the reaction solution was poured into water, extracted with ethyl acetate, washed with water and a saturated sodium chloride aqueous solution, and then dried over anhydrous sodium sulfate. Then, the solvent was distilled off under reduced pressure, and the residue was purified by column chromatography to obtain 2.2 g (yield: 64.7%) of the desired product. Refractive index: 1.5933.

EXAMPLE 6 (Process C)

Preparation of ethyl 5-(4,6-dimethoxypyrimidin-2-yloxy)-3(4-methylphenyl)-2-methylthioimidazole- 4-carboxylate (Compound No. 537)

30 ml of N,N-dimethylformamide was added to 2.0 g (49.7 mmol) of 5(4,6-dimethoxypyrimidin-2-yloxy)-3(4-methylphenyl)-2-methylthioimidazole- 4-carboxylic acid and 0.8 g (5.79 mmol) of potassium carbonate, and the mixture was stirred at room temperature for 30 minutes. 0.9 g (5.77 mmol) of ethyl iodide was added thereto at room temperature, and the mixture was stirred further for 3 hours at room temperature and then poured into water. It was extracted with ethyl acetate, washed with water and a saturated sodium chloride aqueous solution and then dried over anhydrous sodium sulfate. Then, the solvent was distilled off under reduced pressure, and the residue was purified by column chromatography to obtain 1.86 g (yield: 86.9%) of the desired product. Melting point: 147°–148° C.

EXAMPLE 7 (Process D)

Preparation of 4-heptylideneaminoester of 4-(4,6-dimethoxypyrimidin-2-yloxy)-2-phenylfuran-3-carboxylic acid (Compound No. 15)

1.7 g (5.0 mmol) of 4-(4,6-dimethoxypyrimidin-2-yloxy)-2-phenylfuran-3-carboxylic acid was dissolved in 20 ml of N,N-dimethylformamide, and 0.6 g (5.0 mmol) of 4-heptaneoxime and 0.8 g (10.0 mmol) of pyridine were added thereto. The mixture was cooled to 0° C., and 1.0 g (6.0 mmol) of dimethylamidephosphoryl dichloride was gradually dropwise added thereto with stirring. After the dropwise addition, it was stirred at room temperature for 3 hours. The reaction solution was poured into water, extracted with ethyl acetate, washed with water and a saturated sodium chloride aqueous solution and then dried over anhydrous sodium sulfate. Then, the solvent was distilled off under reduced pressure, and the residue was purified by column chromatography to obtain 0.7 g (yield: 31.1%) of the desired product.

EXAMPLE 8 (Process E)

Preparation of 4-(4,6-dimethoxypyrimidin-2-yloxy)-3-methylisothiazole-5-carboxylic acid (Compound No. 480)

2.0 g (6.15 mmol) of ethyl 4-(4,6-dimethoxypyrimidin-2-yloxy)-3-methylisothiazole-5-carboxylate was dissolved in 20 ml of dimethylsulfoxide, and 3.1 ml (6.20 mmol) of a 2N sodium hydroxide aqueous solution was added thereto, followed by stirring at room temperature for 2 hours. The reaction solution was poured into water and adjusted to pH 3 to 4 with dilute hydrochloric acid, whereupon formed precipitates were collected by filtration, washed with water and then dried. Crude crystals were washed with hexane to obtain 1.7 g (yield: 94.4%) of the desired product. Melting point: 139°–141° C.

EXAMPLE 9 (Process F)

Preparation of sodium 3-(4,6-dimethoxypyrimidin-2-yloxy)-5-methylfuran-2-carboxylate (Compound No. 12)

30 ml of water was added to 2.07 ml (4.14 mmol) of a 2N sodium hydroxide aqueous solution, and 1.16 g (4.14 mmol) of 3-(4,6-dimethoxypyrimidin-2-yloxy)-5-methylfuran-2-carboxylic acid was added thereto at room temperature, followed by stirring for one hour. Then, the reaction solution was concentrated under reduced pressure to obtain 1.21 g (yield: 96.8%) of the desired product. Melting point: 225°–229.5° C.

EXAMPLE 10 (Process G)

Preparation of copper salt of 4-(4,6-dimethoxypyrimidin-2-yloxy)isoxazole-3-carboxylic acid (Compound No. 479)

20 ml of water was added to 0.80 ml (1.60 mmol) of a 2N sodium hydroxide aqueous solution, and 0.40 g (1.50 mmol) of 4-(4,6-dimethoxypyrimidin-2-yloxy)isoxazole-3-carboxylic acid was added thereto at room temperature, followed by stirring for 30 minutes. Then, 0.30 g (1.88 mmol) of copper sulfate was dissolved in 10 ml of water and added thereto at room temperature, followed by stirring for 5 minutes. Precipitated crystals were collected by filtration to obtain 0.40 g (yield: 89.7%) of the desired product. Melting point: 148°–152° C.

EXAMPLE 11 (Process H)

Preparation of N-methylsulfonyl 4-(4,6-dimethoxypyrimidin-2-yloxy)-3-methylisothiazole-5-carbonamide (Compound No. 488)

10 ml of N,N-dimethylformamide was added to 0.68 g (2.29 mmol) of 4-(4,6-dimethoxypyrimidin-2-yloxy)-3-methylisothiazole-carboxylic acid and 0.41 g (2.53 mmol) of carbonyldiimidazole, and the mixture was stirred at room temperature for 3 hours. Then, 10 ml of N,N-dimethylformamide was added to 0.43 g (4.52 mmol) of methanesulfonamide and 0.18 g (4.50 mmol) of 60% sodium hydride, and the mixture was heated and stirred at from 80° to 90° C. for 2 hours and then added to the previously prepared dimethylformamide solution of carbonylimidazole at room temperature, and stirring was continued further at room temperature for 3 hours. The reaction solution was poured into water and washed with ethyl acetate. Then, the aqueous layer was acidified with a 10% HCl solution. Precipitated crystals were collected by filtration and washed with isopropyl ether to obtain 0.61 g (yield: 70.9%).

Now, compounds of the present invention are presented in Tables 1 to 60.

TABLE 1

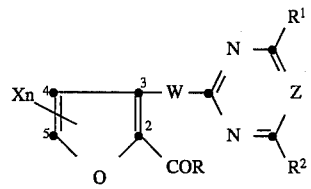

| Comp. No. | Xn | W | Z | R¹ | R² | R | Physical nature mp (°C.) $n_D^{20}$ |
|---|---|---|---|---|---|---|---|
| 1 | H | O | CH | OCH$_3$ | OCH$_3$ | OH | |

TABLE 1-continued

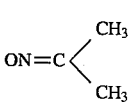

| Comp. No. | Xn | W | Z | R¹ | R² | R | Physical nature mp (°C.) $n_D^{20}$ |
|---|---|---|---|---|---|---|---|
| 2 | 5-CH$_3$ | O | CH | OCH$_3$ | OCH$_3$ | OH | 157–159 |
| 3 | 5-CH$_3$ | O | CH | OCH$_3$ | OCH$_3$ | OC$_2$H$_5$ | 62–72 |
| 4 | 5-CH$_3$ | O | CH | Cl | OCH$_3$ | OH | |
| 5 | 5-CH$_3$ | O | CH | Cl | OCH$_3$ | OCH$_3$ | |
| 6 | H | S | CH | OCH$_3$ | OCH$_3$ | OH | |
| 7 | H | S | CH | OCH$_3$ | OCH$_3$ | OCH$_3$ | |
| 8 | H | S | N | OCH$_3$ | OCH$_3$ | OCH$_3$ | |
| 9 | H | S | N | OCH$_3$ | OCH$_3$ | OH | |
| 10 | H | O | CH | OCH$_3$ | OCH$_3$ | ON=C(CH$_3$)(CH$_3$) | |
| 11 | H | O | CH | OCH$_3$ | OCH$_3$ | NHSO$_2$CH$_3$ | |
| 12 | 5-CH$_3$ | O | CH | OCH$_3$ | OCH$_3$ | ONa | 225–229.5 |

TABLE 2

| Comp. No. | Xn | W | Z | R¹ | R² | R | Physical nature mp (°C.) $n_D^{20}$ |
|---|---|---|---|---|---|---|---|
| 13 | 2-phenyl | O | CH | OCH$_3$ | OCH$_3$ | OH | 97–99 |
| 14 | 2-phenyl | O | CH | OCH$_3$ | OCH$_3$ | OCH$_3$ | |
| 15 | 2-phenyl | O | CH | OCH$_3$ | OCH$_3$ | ON=C(C$_3$H$_7$)(C$_3$H$_7$) | unmeasurable |
| 16 | 2-phenyl | O | CH | Cl | OCH$_3$ | OH | |
| 17 | 2-phenyl | O | CH | N(CH$_3$)(CH$_3$) | OCH$_3$ | OC$_2$H$_5$ | |
| 18 | 2-CH$_3$ | O | CH | OCH$_3$ | OCH$_3$ | OH | |

TABLE 2-continued

[Structure: furan/thiophene ring with Xn at position 2-3, RC(=O) at position 3, W-C(=N-CR1=Z-N=CR2) at position 4, ring atom at position 1 is O]

| Comp. No. | Xn | W | Z | R¹ | R² | R | Physical nature mp (°C.) $n_D^{20}$ |
|---|---|---|---|---|---|---|---|
| 19 | 2-CH₃ | O | CH | OCH₃ | OCH₃ | OC₂H₅ | 86–90 |
| 20 | 2-CH₃ | S | CH | OCH₃ | OCH₃ | OH | |
| 21 | 2-CH₃ | S | CH | Cl | OCH₃ | OCH₃ | |

TABLE 3

[Structure: thiophene ring with Xn substituent, W-C(=N-CR¹=Z-N=CR²) at one position, COR at another, S in ring]

| Comp. No. | Xn | W | Z | R¹ | R² | R | Physical nature mp (°C.) $n_D^{20}$ |
|---|---|---|---|---|---|---|---|
| 22 | H | N | CH | OCH₃ | OCH₃ | OH | 199–200.5 |
| 23 | H | NH | CH | OCH₃ | OCH₃ | OCH₃ | 151–152 |
| 24 | H | N—CH₃ | CH | OCH₃ | OCH₃ | OH | 149–152 |
| 25 | H | N—CH₃ | CH | OCH₃ | OCH₃ | OCH₃ | 76–82 |
| 26 | 4-phenyl | O | CH | OCH₃ | OCH₃ | OH | |
| 27 | 5-(3-Cl-phenyl) | O | CH | OCH₃ | OCH₃ | OH | 154–156 |
| 28 | 5-(3-Cl-phenyl) | O | CH | OCH₃ | OCH₃ | OC₂H₅ | 1.5735 |
| 29 | 4-(3-Cl-phenyl) | O | CH | Cl | OCH₃ | OCH₃ | |
| 30 | 4-(3-Cl-phenyl) | O | CH | Cl | OCH₃ | OH | |

TABLE 3-continued

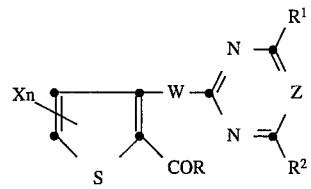

| Comp. No. | Xn | W | Z | R¹ | R² | R | Physical nature mp (°C.) $n_D^{20}$ |
|---|---|---|---|---|---|---|---|
| 31 | 4-(4-Cl-phenyl) | O | CH | $OCHF_2$ | $OCH_3$ | $OCH_3$ | |
| 32 | 4-(4-Cl-phenyl) | O | CH | $OCHF_2$ | $OCH_3$ | OH | |
| 33 | 5-(3-$CF_3$-phenyl) | O | CH | $OCH_3$ | $OCH_3$ | $OC_2H_5$ | 88–90 |
| 34 | 4-(4-$CF_3$-phenyl) | O | CH | $OCH_3$ | $OCH_3$ | OH | |
| 35 | 4-(4-$CF_3$-phenyl) | S | CH | $OCH_3$ | $OCH_3$ | OH | |

TABLE 4

| Comp. No. | Xn | W | Z | R¹ | R² | R | Physical nature mp (°C.) $n_D^{20}$ |
|---|---|---|---|---|---|---|---|
| 36 | 4-(4-$CF_3$-phenyl) | S | CH | $OCH_3$ | $OCH_3$ | $OCH_3$ | |
| 37 | $4\text{-}CH=CH-CH_3$ | O | CH | $OCH_3$ | $OCH_3$ | OH | |
| 38 | $4\text{-}CH=CH-CH_3$ | O | CH | $OCH_3$ | $OCH_3$ | $OC_2H_5$ | 1.5465 |
| 39 | $5\text{-}COOC_2H_5$ | O | CH | $OCH_3$ | $OCH_3$ | $OC_2H_5$ | 1.5445 |
| 40 | 5-COOH | O | CH | $OCH_3$ | $OCH_3$ | OH | 257–262 |
| 41 | $4\text{-}CH_3, 5\text{-}COOC_2H_5$ | O | CH | $OCH_3$ | $OCH_3$ | $OC_2H_5$ | 90–93 |
| 42 | $4\text{-}CH_3, 5\text{-}COOC_2H_5$ | O | CH | $OCH_3$ | $OCH_3$ | $OCH_3$ | |
| 43 | H | S | CH | $OCH_3$ | $OCH_3$ | OH | |
| 44 | H | S | CH | $OCH_3$ | $OCH_3$ | $OCH_3$ | |

TABLE 4-continued

| Comp. No. | Xn | W | Z | $R^1$ | $R^2$ | R | Physical nature mp (°C.) $n_D^{20}$ |
|---|---|---|---|---|---|---|---|
| 45 | H | S | CH | $OCH_3$ | $OCH_3$ | $OC_2H_5$ | |
| 46 | 5-$CH_3$ | O | CH | $OCH_3$ | $OCH_3$ | $OCH_3$ | |
| 47 | 5-$CH_3$ | O | CH | $OCH_3$ | $OCH_3$ | OH | |
| 48 | 5-$CH(CH_3)_2$ | O | CH | $OCH_3$ | $OCH_3$ | $OCH_3$ | |
| 49 | 5-$CH(CH_3)_2$ | O | CH | $OCH_3$ | $OCH_3$ | OH | |
| 50 | 5—(phenyl) | O | CH | $OCH_3$ | $OCH_3$ | $OCH_3$ | |
| 51 | 5—(phenyl) | O | CH | $OCH_3$ | $OCH_3$ | OH | |
| 52 | 5-$C(CH_3)_3$ | O | CH | $OCH_3$ | $OCH_3$ | $OCH_3$ | |
| 53 | 5-$C(CH_3)_3$ | O | CH | $OCH_3$ | $OCH_3$ | OH | |
| 54 | 5—(naphthyl) | O | CH | $OCH_3$ | $OCH_3$ | $OCH_3$ | |
| 55 | 5—(naphthyl) | O | CH | $OCH_3$ | $OCH_3$ | OH | |

TABLE 5

| Comp. No. | Xn | W | Z | $R^1$ | $R^2$ | R | Physical nature mp (°C.) $n_D^{20}$ |
|---|---|---|---|---|---|---|---|
| 56 | 5-Cl | O | CH | $OCH_3$ | $OCH_3$ | $OC_3H_7$ | |
| 57 | 5-Cl | O | CH | $OCH_3$ | $OCH_3$ | OH | |
| 58 | 4-Cl | O | CH | $OCH_3$ | $OCH_3$ | $OCH_3$ | |
| 59 | 4-Cl | O | CH | $OCH_3$ | $OCH_3$ | OH | |
| 60 | 4,5-$Cl_2$ | O | CH | $OCH_3$ | $OCH_3$ | $OCH_3$ | |
| 61 | 4,5-$Cl_2$ | O | CH | $OCH_3$ | $OCH_3$ | OH | |
| 62 | 5-$C_2F_5$ | O | CH | $OCH_3$ | $OCH_3$ | $OCH_3$ | |
| 63 | 5-$C_2F_5$ | O | CH | $OCH_3$ | $OCH_3$ | OH | |
| 64 | H | NCHO | CH | $OCH_3$ | $OCH_3$ | $OCH_3$ | |
| 65 | H | NCHO | CH | $OCH_3$ | $OCH_3$ | OH | |
| 66 | H | $NCH_2CH=CH_2$ | CH | $OCH_3$ | $OCH_3$ | $OCH_3$ | |
| 67 | H | $NCH_2CH=CH_2$ | CH | $OCH_3$ | $OCH_3$ | OH | |
| 68 | H | $NCH_2C\equiv CH$ | CH | $OCH_3$ | $OCH_3$ | $OC_2H_5$ | |
| 69 | H | $NCH_2C\equiv CH$ | CH | $OCH_3$ | $OCH_3$ | OH | |
| 70 | H | $NCH_2OCH_3$ | CH | $OCH_3$ | $OCH_3$ | $OCH_3$ | |
| 71 | H | $NCH_2OCH_3$ | CH | $OCH_3$ | $OCH_3$ | OH | |
| 72 | H | $NSO_2CH_3$ | CH | $OCH_3$ | $OCH_3$ | $OC_2H_5$ | |
| 73 | H | $NSO_2CH_3$ | CH | $OCH_3$ | $OCH_3$ | OH | |
| 74 | H | $NCOCH_3$ | CH | $OCH_3$ | $OCH_3$ | $OCH_3$ | |
| 75 | H | $NCOCH_3$ | CH | $OCH_3$ | $OCH_3$ | OH | |

TABLE 5-continued

| Comp. No. | Xn | W | Z | R¹ | R² | R | Physical nature mp (°C.) $n_D^{20}$ |
|---|---|---|---|---|---|---|---|
| 76 | H | N—CO—(phenyl) | CH | $OCH_3$ | $OCH_3$ | $OCH_3$ | |
| 77 | H | N—CO—(phenyl) | CH | $OCH_3$ | $OCH_3$ | OH | |
| 78 | H | N—CO—(2-Cl-phenyl) | CH | $OCH_3$ | $OCH_3$ | $OCH_3$ | |
| 79 | H | N—CO—(2-Cl-phenyl) | CH | $OCH_3$ | $OCH_3$ | OH | |

TABLE 6

| Comp. No. | Xn | W | Z | R¹ | R² | R | Physical nature mp (°C.) $n_D^{20}$ |
|---|---|---|---|---|---|---|---|
| 80 | H | NH | CH | $OCH_3$ | cyclopropyl | OK | |
| 81 | H | NH | CH | $OCH_3$ | cyclopropyl | O½Ca | |
| 82 | H | NH | CH | $OCH_3$ | cyclopropyl | $ONH_3CH(CH_3)_2$ | |
| 83 | H | NH | CH | $OCH_3$ | cyclopropyl | $ONH_4$ | |
| 84 | H | NH | CH | $OCH_3$ | cyclopropyl | O⅓Fe | |
| 85 | H | NH | CH | $OCH_3$ | cyclopropyl | $NHSO_2CH_3$ | |
| 86 | H | NH | CH | $OCH_3$ | $CF_3$ | $OCH_3$ | |
| 87 | H | NH | CH | $OCH_3$ | $CF_3$ | OH | |
| 88 | H | NH | CH | $OCH_3$ | $CF_3$ | $OCH_2CH_2Si(CH_3)_3$ | |
| 89 | H | NH | CH | $OCH_3$ | $SCH_3$ | $OC_2H_5$ | |
| 90 | H | NH | CH | $OCH_3$ | $SCH_3$ | OH | |
| 91 | H | NH | CH | $OCH_3$ | $SCH_3$ | $OCH_2CH_2Si(CH_3)_3$ | |
| 92 | H | NH | CH | $OCH_3$ | $SCH_3$ | $OCH_2$—(phenyl)—$OCH_3$ | |
| 93 | H | NH | CH | $OCH_3$ | $CH_2OCH_3$ | $OCH_3$ | |
| 94 | H | NH | CH | $OCH_3$ | $CH_2OCH_3$ | OH | |
| 95 | H | NH | CH | $OCH_3$ | $CH_2OCH_3$ | $OCH_2CH_2Si(CH_3)_3$ | |

TABLE 7

| Comp. No. | Xn | W | Z | R¹ | R² | R | Physical nature mp (°C.) $n_D^{20}$ |
|---|---|---|---|---|---|---|---|
| 96 | H | NH | CH | CH₃ | CH₃ | OC₄H₉ | |
| 97 | H | NH | CH | CH₃ | CH₃ | OH | |
| 98 | H | NH | CH | CH₃ | CH₃ | OCH₂–C₆H₄–OCH₃ | |
| 99 | H | NH | CH | CH₃ | –C≡C–CH₃ | OCH₃ | |
| 100 | H | NH | CH | CH₃ | –C≡C–CH₃ | OH | |
| 101 | H | NH | CH | CH₃ | –C≡C–CH₃ | NHOCH₂CH=CH₂ | |
| 102 | H | NH | CH | CH₃ | –C≡C–CH₃ | N(SO₂CH₃)(OCH₂CH=CH₂) | |
| 103 | H | NH | CH | OCH₃ | OCH₂C≡–CH | OCH₃ | |
| 104 | H | NH | CH | OCH₃ | OCH₂C≡–CH | OH | |
| 105 | H | NH | CH | OCH₃ | OCH₂C≡–CH | OCH₂–C₆H₄–OCH₃ | |
| 106 | H | NH | CH | OCH₃ | OCH₂CH=CH₂ | OCH₃ | |
| 107 | H | NH | CH | OCH₃ | OCH₂CH=CH₂ | OH | |
| 108 | H | NH | CH | OCH₃ | OCH₂CH=CH₂ | OCH₂CH₂Si(CH₃)₃ | |
| 109 | H | NH | CH | OCH₃ | CH₂SCH₃ | OC₂H₅ | |
| 110 | H | NH | CH | OCH₃ | CH₂SCH₃ | OH | |
| 111 | H | NH | CH | OCH₃ | CH₂SCH₃ | OCH₂–C₆H₄–OCH₃ | |
| 112 | H | NH | CH | OCH₃ | NHCH₃ | OCH₃ | |
| 113 | H | NH | CH | OCH₃ | NHCH₃ | OH | |

TABLE 8

| Comp. No. | Xn | W | Z | R¹ | R² | R | Physical nature mp (°C.) $n_D^{20}$ |
|---|---|---|---|---|---|---|---|
| 114 | H | NH | N | OCH₃ | OCH₃ | OCH₃ | 190–192 |
| 115 | H | NH | N | OCH₃ | OCH₃ | OH | |
| 116 | H | NH | N | OCH₃ | OCH₃ | NHSO₂CH₃ | |
| 117 | H | NH | N | OCH₃ | OCH₃ | NHSO₂–C₆H₅ | |
| 118 | H | NH | N | OCH₃ | OCH₃ | NHSO₂–(2-Cl-C₆H₄) | |

TABLE 8-continued

| Comp. No. | Xn | W | Z | R¹ | R² | R | Physical nature mp (°C.) $n_D^{20}$ |
|---|---|---|---|---|---|---|---|
| 119 | H | NH | N | OCH₃ | OCH₃ | 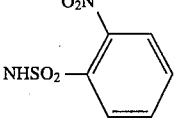 | |
| 120 | H | NH | N | OCH₃ | OCH₃ | 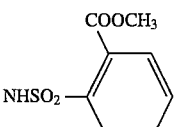 | |
| 121 | H | NH | N | OCH₃ | OCH₃ | OCH₂CH₂Si(CH₃)₃ | |
| 122 | H | NH | N | CH₃ | OCH₃ | OC₂H₅ | |
| 123 | H | NH | N | CH₃ | OCH₃ | OH | |
| 124 | H | NH | N | CH₃ | OCH₃ | NHSO₂C₂H₅ | |
| 125 | H | NH | N | CH₃ | OCH₃ | 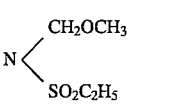 | |
| 126 | H | NH | N | CH₃ | OCH₃ | OCH₂CH₂Si(CH₃)₃ | |
| 127 | H | NH | N | CH₃ | OCH₃ | 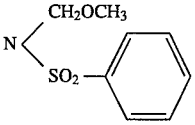 | |
| 128 | H | NH | N | CH₃ | OCH₃ | 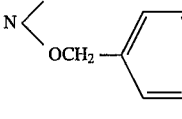 | |
| 129 | H | NH | N | CH₃ | OCH₃ | 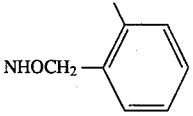 | |

TABLE 9

| Comp. No. | Xn | W | Z | R¹ | R² | R | Physical nature mp (°C.) $n_D^{20}$ |
|---|---|---|---|---|---|---|---|
| 130 | H | NH | N | OCHF₂ | OCH₃ | OCH₃ | |
| 131 | H | NH | N | OCHF₂ | OCH₃ | OH | |
| 132 | H | NH | N | OCHF₂ | OCH₃ | OCH₂CH₂Si(CH₃)₃ | |
| 133 | H | NH | N | OCHF₂ | OCH₃ | NHOCH₃ | |
| 134 | H | NH | N | OCHF₂ | OCH₃ | 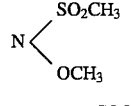 | |
| 135 | H | NH | N | OCHF₂ | OCH₃ | 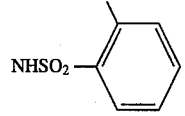 | |

TABLE 9-continued

| Comp. No. | Xn | W | Z | R¹ | R² | R | Physical nature mp (°C.) $n_D^{20}$ |
|---|---|---|---|---|---|---|---|
| 136 | H | NH | N | OCHF$_2$ | OCH$_3$ | NHCH$_2$C≡CH | |
| 137 | H | NH | N | OCHF$_2$ | OCH$_3$ | NHOCH$_2$CH=CH$_2$ | |
| 138 | H | NH | CH | OCHF$_2$ | OCHF$_2$ | OC$_2$H$_5$ | |
| 139 | H | NH | CH | OCHF$_2$ | OCHF$_2$ | OH | |
| 140 | H | NH | CH | OCHF$_2$ | OCHF$_2$ | OCH$_2$CH$_2$Si(CH$_3$)$_3$ | |
| 141 | H | NH | CH | OCHF$_2$ | OCHF$_2$ | NHSO$_2$CH$_3$ | |
| 142 | H | NH | CH | OCHF$_2$ | OCHF$_2$ | N(CH$_2$OCH$_3$)(SO$_2$CH$_3$) | |
| 143 | H | NH | CH | OCHF$_2$ | OCHF$_2$ | NHOCH$_2$COOCH$_3$ | |
| 144 | H | NH | CH | OCHF$_2$ | OCHF$_2$ | N(OCH$_2$COOCH$_3$)(SO$_2$CH$_3$) | |
| 145 | H | NH | CH | OCHF$_2$ | OCHF$_2$ | ONa | |
| 146 | H | NH | CH | OCH$_3$ | 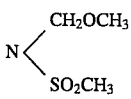 | OC$_3$H$_7$ | |
| 147 | H | NH | CH | OCH$_3$ | 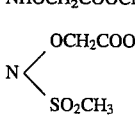 | OH | |
| 148 | H | NH | N | OCH$_3$ | CF$_3$ | OC$_2$H$_5$ | |
| 149 | H | NH | N | OCH$_3$ | CF$_3$ | OH | |

TABLE 10

| Comp. No. | Xn | W | Z | R¹ | R² | R | Physical nature mp (°C.) $n_D^{20}$ |
|---|---|---|---|---|---|---|---|
| 150 | 4-CH$_3$ | NH | CH | OCH$_3$ | OCH$_3$ | OH | 92–96 |
| 151 | 4-CH$_3$ | NH | CH | OCH$_3$ | OCH$_3$ | OC$_2$H$_5$ | 126–128 |
| 152 | 4-CH$_3$ | NCHO | CH | Cl | OCH$_3$ | OCH$_3$ | |
| 153 | 4-CH$_3$ | N—CH$_3$ | CH | OCH$_3$ | OCH$_3$ | OH | 156–159 |
| 154 | 4-CH$_3$ | N—CH$_3$ | CH | OCH$_3$ | OCH$_3$ | OC$_2$H$_5$ | 1.5487 |
| 155 | 4-CH$_3$ | O | CH | OCH$_3$ | OCH$_3$ | OH | |
| 156 | 4-CH$_3$ | O | CH | OCH$_3$ | OCH$_3$ | OCH$_3$ | |
| 157 | H | O | CH | OCH$_3$ | OCH$_3$ | OC$_2$H$_5$ | 37–45 |
| 158 | H | O | CH | Cl | OCH$_3$ | OH | |
| 159 | H | O | CH | Cl | OCH$_3$ | OC$_2$H$_5$ | |
| 160 | H | O | CH | OCHF$_2$ | OCH$_3$ | OH | |
| 161 | H | O | CH | OCHF$_2$ | OCH$_3$ | OCH$_3$ | |
| 162 |  | O | CH | OCH$_3$ | OCH$_3$ | OH | |
| 163 | 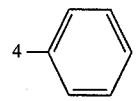 | O | CH | OCH$_3$ | OCH$_3$ | OC$_2$H$_5$ | |

TABLE 11

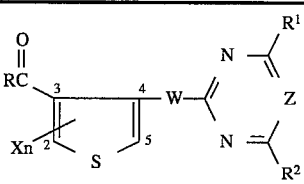

| Comp. No. | Xn | W | Z | R¹ | R² | R | Physical nature mp (°C.) $n^{20}_D$ |
|---|---|---|---|---|---|---|---|
| 164 | 2-NHC(O)-C₆H₅ | O | CH | OCH₃ | OCH₃ | OH | 182–186 |
| 165 | 2-NHC(O)-C₆H₅ | O | CH | OCH₃ | OCH₃ | OC₂H₅ | 161–165 |
| 166 | 2-NHC(O)-C₆H₃(3-Cl, 4-Cl) | O | CH | OCH₃ | OCH₃ | OH | |
| 167 | 2-NHC(O)-C₆H₃(3-Cl, 4-Cl) | O | CH | OCH₃ | OCH₃ | OCH₃ | |
| 168 | 2-SO₂CH₃ | O | CH | OCH₃ | OCH₃ | OH | 172–184 |
| 169 | 2-CH₂SCH₃ | O | CH | OCH₃ | OCH₃ | OH | 133–135 |
| 170 | 2-CH₂SCH₃ | O | CH | OCH₃ | OCH₃ | OC₂H₅ | unmeasurable |
| 171 | 2-CH₃, 5-C₆H₅ | O | CH | OCH₃ | OCH₃ | OH | 183–184 |
| 172 | 2-CH₃, 5-C₆H₅ | O | CH | OCH₃ | OCH₃ | OC₅H₃ | 83–85 |
| 173 | 2-C₆H₅, 5-C₆H₅ | O | CH | OCH₃ | OCH₃ | OH | 90–92 |
| 174 | 2-C₆H₅, 5-C₆H₅ | O | CH | OCH₃ | OCH₃ | OC₂H₅ | unmeasurable |
| 175 | 2-CH₃, 5-CH₃ | O | CH | OCH₃ | OCH₃ | OC₂H₅ | 1.5442 |
| 176 | 2-C₆H₅, 5-CH₃ | O | CH | OCH₃ | OCH₃ | OC₂H₅ | 1.5838 |
| 177 | 2-(pyridyl) | O | CH | OCH₃ | OCH₃ | OC₂H₅ | 43–47 |

TABLE 12

| Comp. No. | Xn | W | Z | R¹ | R² | R | Physical nature mp (°C.) $n_D^{20}$ |
|---|---|---|---|---|---|---|---|
| 178 | 2-(4-Cl-C₆H₄) | O | CH | Cl | OCH₃ | OH | |
| 179 | 2-(4-Cl-C₆H₄) | O | CH | Cl | OCH₃ | OCH₃ | |
| 180 | 2-(4-Cl-C₆H₄) | S | CH | OCH₃ | OCH₃ | OH | |
| 181 | 2-(4-Cl-C₆H₄) | S | CH | OCH₃ | OCH₃ | OCH₃ | |
| 182 | 2-(4-Cl-C₆H₄) | NH | CH | OCH₃ | OCH₃ | OH | |
| 183 | 2-(4-Cl-C₆H₄) | NH | CH | OCH₃ | OCH₃ | OCH₃ | |
| 184 | 2-(4-Cl-C₆H₄) | N—CH₃ | CH | OCH₃ | OCH₃ | OH | |
| 185 | 2-(4-Cl-C₆H₄) | N—CH₃ | CH | OCH₃ | OCH₃ | OCH₃ | |
| 186 | 2-(4-Cl-C₆H₄) | O | N | OCH₃ | OCH₃ | OH | |
| 187 | 2-(4-Cl-C₆H₄) | O | N | OCH₃ | OCH₃ | OCH₃ | |
| 188 | 2-(4-Cl-C₆H₄) | O | CH | OCHF₂ | OCH₃ | OH | |
| 189 | 2-(4-Cl-C₆H₄) | O | CH | OCHF₂ | OCH₃ | OCH₃ | |
| 190 | 2-(4-Cl-C₆H₄) | O | CH | OCHF₂ | OCHF₂ | OH | |
| 191 | 2-CH(CH₃)₂ | S | CH | OCH₃ | OCH₃ | OH | |
| 192 | 2-CH(CH₃)₂ | S | CH | OCH₃ | OCH₃ | OCH₃ | |
| 193 | 2-CH(CH₃)₂ | S | CH | Cl | OCH₃ | OH | |
| 194 | 2-CH(CH₃)₂ | S | CH | Cl | OCH₃ | OCH₃ | |

TABLE 13

| Comp. No. | Xn | W | Z | R¹ | R² | R | Physical nature mp (°C.) $n^{20}_D$ |
|---|---|---|---|---|---|---|---|
| 195 | 2—C₆H₄—CH₃ (4-) | O | CH | Cl | OCH₃ | OH | |
| 196 | 2—C₆H₄—CH₃ (4-) | S | CH | OCH₃ | OCH₃ | OH | |
| 197 | 2—C₆H₄—CH₃ (4-) | NH | CH | OCH₃ | OCH₃ | OH | |
| 198 | 2—C₆H₄—CH₃ (4-) | N—CH₃ | CH | OCH₃ | OCH₃ | OH | |
| 199 | 2—C₆H₄—CH₃ (4-) | O | N | OCH₃ | OCH₃ | OH | |
| 200 | 2—C₆H₄—CH₃ (4-) | O | N | CH₃ | OCH₃ | OH | |
| 201 | 2—C₆H₄—CH₃ (4-) | O | CH | CH₃ | CH₃ | OCH₃ | |
| 202 | 2—C₆H₅ | NH | CH | OCH₃ | OCH₃ | OCH₃ | |
| 203 | 2—C₆H₅ | NH | CH | OCH₃ | OCH₃ | OH | |

TABLE 13-continued

| Comp. No. | Xn | W | Z | R¹ | R² | R | Physical nature mp (°C.) $n^{20}_D$ |
|---|---|---|---|---|---|---|---|
| 204 | 2-phenyl | N—CH$_3$ | CH | OCH$_3$ | OCH$_3$ | OCH$_3$ | |
| 205 | 2-phenyl | N—CH$_3$ | CH | OCH$_3$ | OCH$_3$ | OH | |
| 206 | 2-phenyl | O | CH | CH$_3$ | OCH$_3$ | OC$_2$H$_5$ | |
| 207 | 2-phenyl | O | CH | CH$_3$ | OCH$_3$ | OH | |
| 208 | 2-phenyl | O | CH | CH$_3$ | CH$_3$ | OC$_3$H$_7$ | |
| 209 | 2-phenyl | O | CH | CH$_3$ | CH$_3$ | OH | |

TABLE 14

| Comp. No. | Xn | W | Z | R¹ | R² | R | Physical nature mp (°C.) $n^{20}_D$ |
|---|---|---|---|---|---|---|---|
| 210 | 2-phenyl | O | CH | OCH$_3$ | OCH$_3$ | OCH$_2$CH=CH$_2$ | |
| 211 | 2-phenyl | O | CH | OCH$_3$ | OCH$_3$ | OCH$_2$C≡CH | |
| 212 | 2-phenyl | O | CH | OCH$_3$ | OCH$_3$ | OCH$_3$-phenyl | |

TABLE 14-continued

| Comp. No. | Xn | W | Z | R¹ | R² | R | Physical nature mp (°C.) $n^{20}_D$ |
|---|---|---|---|---|---|---|---|
| 213 | 2-phenyl | O | CH | OCH$_3$ | OCH$_3$ | OCH$_2$-C$_6$H$_4$-CH$_3$ | |
| 214 | 2-phenyl | O | CH | OCH$_3$ | OCH$_3$ | OC$_2$H$_5$ | |
| 215 | 2-phenyl | O | CH | OCH$_3$ | OCH$_3$ | O-cyclohexyl | |
| 216 | 2-phenyl | O | CH | OCH$_3$ | OCH$_3$ | O-cyclopentyl | |
| 217 | 2-phenyl | O | CH | OCH$_3$ | OCH$_3$ | SCH$_2$-C$_6$H$_5$ | |
| 218 | 2-phenyl | O | CH | OCH$_3$ | OCH$_3$ | SCH$_2$-C$_6$H$_4$-Cl | |
| 219 | 2-phenyl | O | CH | OCH$_3$ | OCH$_3$ | S-cyclopentyl | |
| 220 | 2-phenyl | O | CH | OCH$_3$ | OCH$_3$ | OCH$_2$OCH$_3$ | |
| 221 | 2-phenyl | O | CH | OCH$_3$ | OCH$_3$ | 2-furyloxy (furan-2-yl-O) | |
| 222 | 2-phenyl | O | CH | OCH$_3$ | OCH$_3$ | tetrahydrofuran-2-yl-O | |
| 223 | 2-phenyl | O | CH | OCH$_3$ | OCH$_3$ | O-C$_6$H$_5$ | |

TABLE 15

| Comp. No. | Xn | W | Z | R¹ | R² | R | Physical nature mp (°C.) $n^{20}_D$ |
|---|---|---|---|---|---|---|---|
| 224 | 2-phenyl | O | CH | OCH₃ | OCH₃ | O-(2-methylphenyl) | |
| 225 | 2-phenyl | O | CH | OCH₃ | OCH₃ | O-(4-chlorophenyl) | |
| 226 | 2-phenyl | O | CH | OCH₃ | OCH₃ | OCH₂CH₂-phenyl | |
| 227 | 2-phenyl | O | CH | OCH₃ | OCH₃ | OCH₂SCH₃ | |
| 228 | 2-phenyl | O | CH | OCH₃ | OCH₃ | OCH₂CN | |
| 229 | 2-phenyl | O | CH | OCH₃ | OCH₃ | OCH₂COOC₂H₅ | |
| 230 | 2-phenyl | O | CH | OCH₃ | OCH₃ | OCH₂CH₂COOCH₃ | |
| 231 | 2-phenyl | O | CH | OCH₃ | OCH₃ | ON=C(cyclopentyl) | |
| 232 | 2-phenyl | O | CH | OCH₃ | OCH₃ | ON=C(tetrahydropyran) | |
| 233 | 2-phenyl | O | CH | OCH₃ | OCH₃ | NHSO₂C₂H₅ | |
| 234 | 2-phenyl | O | CH | OCH₃ | OCH₃ | NHSO₂-phenyl | |
| 235 | 2-phenyl | O | CH | OCH₃ | OCH₃ | NHSO₂-(2-chlorophenyl) | |
| 236 | 2-phenyl | O | CH | OCH₃ | OCH₃ | OCH₂CH₂Si(CH₃)₃ | |

TABLE 15-continued

| Comp. No. | Xn | W | Z | R¹ | R² | R | Physical nature mp (°C.) $n^{20}_D$ |
|---|---|---|---|---|---|---|---|
| 237 | 2-phenyl | O | CH | OCH₃ | OCH₃ | NH₂ | |

TABLE 16

| Comp. No. | Xn | W | Z | R¹ | R² | R | Physical nature mp (°C.) $n^{20}_D$ |
|---|---|---|---|---|---|---|---|
| 238 | 2-phenyl | O | CH | OCH₃ | OCH₃ | NHOH | |
| 239 | 2-phenyl | O | CH | OCH₃ | OCH₃ | NHOC₂H₅ | |
| 240 | 2-phenyl | O | CH | OCH₃ | OCH₃ | N(OCH₃)(CH₃) | |
| 241 | 2-phenyl | O | CH | OCH₃ | OCH₃ | N(OCH₃)(CH₂CH=CH₂) | |
| 242 | 2-phenyl | O | CH | OCH₃ | OCH₃ | N(CH₂OCH₃)(SO₂CH₃) | |
| 243 | 2-phenyl | O | CH | OCH₃ | OCH₃ | OCH₂CH₂N(CH₃)₂ | |
| 244 | 2-phenyl | O | CH | OCH₃ | OCH₃ | SCH₂CH₂N(CH₃)₂ | |

TABLE 17

| Comp. No. | Xn | W | Z | R¹ | R² | R | Physical nature mp (°C.) $n^{20}_D$ |
|---|---|---|---|---|---|---|---|
| 245 | 2-phenyl | O | CH | OCH₃ | OCH₃ | N(OC₂H₅)(SO₂CH₃) | |
| 246 | 2-phenyl | O | CH | OCH₃ | OCH₃ | N(OCH₃)(SO₂C₂H₅) | |

TABLE 17-continued

| Comp. No. | Xn | W | Z | R¹ | R² | R | Physical nature mp (°C.) $n^{20}_D$ |
|---|---|---|---|---|---|---|---|
| 247 | 2-C₆H₅ | O | CH | OCH₃ | OCH₃ | N(OCH₃)(SO₂C₆H₅) | |
| 248 | 2-C₆H₅ | O | CH | OCH₃ | OCH₃ | N(OCH₃)(SO₂-C₆H₄-CH₃) | |
| 249 | 2-C₆H₅ | O | CH | OCH₃ | OCH₃ | N(OCH₂CH=CH₂)(SO₂CH₃) | |
| 250 | 2-C₆H₅ | O | CH | OCH₃ | OCH₃ | NH-C₆H₅ | |
| 251 | 2-C₆H₅ | O | CH | OCH₃ | OCH₃ | NH-(2-Cl-C₆H₄) | |
| 252 | 2-C₆H₅ | O | CH | OCH₃ | OCH₃ | N(COCH₃)(C₆H₅) | |
| 253 | 2-C₆H₅ | O | CH | OCH₃ | OCH₃ | NH-C₆H₁₁ | |
| 254 | 2-C₆H₅ | O | CH | OCH₃ | OCH₃ | NHCH₂CH₂OCH₃ | |
| 255 | 2-C₆H₅ | O | CH | OCH₃ | OCH₃ | NHCOCH₃ | |

TABLE 18

| Comp. No. | Xn | W | Z | R¹ | R² | R | Physical nature mp (°C.) $n^{20}_D$ |
|---|---|---|---|---|---|---|---|
| 256 | 2-phenyl | O | CH | OCH₃ | OCH₃ | NHCH₂CH=CH₂ | |
| 257 | 2-phenyl | O | CH | OCH₃ | OCH₃ | NHCH₂C≡CH | |
| 258 | 2-phenyl | O | CH | OCH₃ | OCH₃ | NHOCH₂CH=CH₂ | |
| 259 | 2-phenyl | O | CH | OCH₃ | OCH₃ | NHOCH₂C≡CH | |
| 260 | 2-phenyl | O | CH | OCH₃ | OCH₃ | NHOCH₂–phenyl | |
| 261 | 2-phenyl | O | CH | OCH₃ | OCH₃ | NHOCH₂–(2-Cl-phenyl) | |
| 262 | 2-phenyl | O | CH | OCH₃ | OCH₃ | NHCH₂C(=O)CH₃ | |
| 263 | 2-phenyl | O | CH | OCH₃ | OCH₃ | NHOCH₂COOC₂H₅ | |
| 264 | 2-phenyl | O | CH | OCH₃ | OCH₃ | N(SO₂CH₃)(OCH₂C≡CH) | |
| 265 | 2-phenyl | O | CH | OCH₃ | OCH₃ | N(SO₂CH₃)(OCH₂COOCH₃) | |
| 266 | 2-phenyl | O | CH | OCH₃ | OCH₃ | N(SO₂CH₃)(OCH₂–phenyl) | |
| 267 | 2-phenyl | O | CH | OCH₃ | OCH₃ | N(SO₂CH₃)(OCH₂–(2-Cl-phenyl)) | |

TABLE 19

| Comp. No. | Xn | W | Z | R¹ | R² | R | Physical nature mp (°C.) $n^{20}_D$ |
|---|---|---|---|---|---|---|---|
| 268 | 2-phenyl | O | CH | OCH$_3$ | OCH$_3$ | NHNH$_2$ | |
| 269 | 2-phenyl | O | CH | OCH$_3$ | OCH$_3$ | NHNHCOCH$_3$ | |
| 270 | 2-phenyl | O | CH | OCH$_3$ | OCH$_3$ | NHNH-phenyl | |
| 271 | 2-phenyl | O | CH | OCH$_3$ | OCH$_3$ | piperidinyl | |
| 272 | 2-phenyl | O | CH | OCH$_3$ | OCH$_3$ | morpholinyl | |
| 273 | 2-phenyl | O | N | OCH$_3$ | OCH$_3$ | OCH$_2$-phenyl | |
| 274 | 2-phenyl | O | N | OCH$_3$ | OCH$_3$ | OCH$_2$-(4-CH$_3$-phenyl) | |
| 275 | 2-phenyl | O | N | OCH$_3$ | OCH$_3$ | NHSO$_2$-(2-Cl-phenyl) | |
| 276 | 2-phenyl | O | N | OCH$_3$ | OCH$_3$ | NHSO$_2$C$_2$H$_5$ | |
| 277 | 2-phenyl | O | N | OCH$_3$ | OCH$_3$ | N(CH$_2$OCH$_3$)(SO$_2$CH$_3$) | |
| 278 | 2-phenyl | O | N | OCH$_3$ | OCH$_3$ | N(OC$_2$H$_5$)(SO$_2$CH$_3$) | |

TABLE 20

| Comp. No. | Xn | W | Z | R¹ | R² | R | Physical nature mp (°C.) $n^{20}_D$ |
|---|---|---|---|---|---|---|---|
| 279 | 2-phenyl | O | CH | Cl | OCH₃ | OC₂H₅ | |
| 280 | 2-phenyl | O | CH | Cl | OCH₃ | OH | |
| 281 | 2-phenyl | O | CH | Cl | OCH₃ | OCH₂CH₂Si(CH₃)₃ | |
| 282 | 2-phenyl | O | CH | Cl | OCH₃ | OCH₂-phenyl | |
| 283 | 2-phenyl | O | CH | Cl | OCH₃ | OCH₂OCH₃ | |
| 284 | 2-phenyl | O | CH | Cl | OCH₃ | ON=C(CH₃)₂ | |
| 285 | 2-phenyl | O | CH | Cl | OCH₃ | NHSO₂CH₃ | |
| 286 | 2-phenyl | O | CH | Cl | OCH₃ | NHOCH₂CH=CH₂ | |
| 287 | 2-phenyl | O | CH | Cl | OCH₃ | N(SO₂CH₃)(OCH₂CH=CH₂) | |
| 288 | 2-phenyl | O | CH | Cl | OCH₃ | OCH₂-(4-OCH₃-phenyl) | |
| 289 | 2-phenyl | O | CH | Cl | OCH₃ | N(SO₂CH₃)(CH₂OCH₃) | |
| 290 | 2-phenyl | O | CH | Cl | OCH₃ | -N(imidazole) | |
| 291 | 2-phenyl | O | CH | Cl | OCH₃ | N(SO₂CH₃)(CH₃) | |

TABLE 21

| Comp. No. | Xn | W | Z | R¹ | R² | R | Physical nature mp (°C.) $n_D^{20}$ |
|---|---|---|---|---|---|---|---|
| 292 | 2-C₆H₅ | O | CH | Cl | OCH₃ | N(OCH₃)(CH₃) | |
| 293 | 2-C₆H₅ | O | CH | Cl | OCH₃ | SC₂H₅ | |
| 294 | 2-C₆H₅ | O | CH | Cl | OCH₃ | SCH₂-C₆H₅ | |
| 295 | 2-C₆H₅ | O | CH | Cl | OCH₃ | O-cyclopentyl | |
| 296 | 2-C₆H₅ | O | CH | Cl | OCH₃ | S-C₆H₅ | |
| 297 | 2-C₆H₅ | O | CH | Cl | OCH₃ | O-furyl | |
| 298 | 2-C₆H₅ | O | CH | Cl | OCH₃ | O-tetrahydrofuryl | |
| 299 | 2-C₆H₅ | O | CH | Cl | OCH₃ | O-C₆H₅ | |
| 300 | 2-C₆H₅ | O | CH | Cl | OCH₃ | O-(2-CH₃)C₆H₄ | |
| 301 | 2-C₆H₅ | O | CH | Cl | OCH₃ | O-(4-Cl)C₆H₄ | |
| 302 | 2-C₆H₅ | O | CH | Cl | OCH₃ | OCH₂CH₂-C₆H₅ | |
| 303 | 2-C₆H₅ | O | CH | Cl | OCH₃ | OCH₂COOCH₃ | |
| 304 | 2-C₆H₅ | O | CH | Cl | OCH₃ | NHOCH₂COOC₂H₅ | |

TABLE 21-continued

| Comp. No. | Xn | W | Z | R¹ | R² | R | Physical nature mp (°C.) $n^{20}_D$ |
|---|---|---|---|---|---|---|---|
| 305 | 2-phenyl | O | CH | Cl | OCH₃ | ON=C(cyclohexylidene) | |
| 306 | 2-phenyl | O | CH | Cl | OCH₃ | NHSO₂-phenyl | |

TABLE 22

| Comp. No. | Xn | W | Z | R¹ | R² | R | Physical nature mp (°C.) $n^{20}_D$ |
|---|---|---|---|---|---|---|---|
| 307 | 2-phenyl | O | CH | Cl | OCH₃ | NHSO₂-(2-Cl-phenyl) | |
| 308 | 2-phenyl | O | CH | Cl | OCH₃ | NHOH | |
| 309 | 2-phenyl | O | CH | Cl | OCH₃ | NHCH₂C≡CH | |
| 310 | 2-phenyl | O | CH | Cl | OCH₃ | NHOCH₂C≡CH | |
| 311 | 2-phenyl | O | CH | Cl | OCH₃ | NHNH₂ | |
| 312 | 2-phenyl | O | CH | Cl | OCH₃ | NHNHCOCH₃ | |
| 313 | 2-phenyl | O | CH | Cl | OCH₃ | NHNH-phenyl | |
| 314 | 2-phenyl | O | CH | Cl | OCH₃ | NHN(CH₃)₂ | |
| 315 | 2-phenyl | O | CH | Cl | OCH₃ | NHCOCH₃ | |

TABLE 22-continued

| Comp. No. | Xn | W | Z | R¹ | R² | R | Physical nature mp (°C.) $n_D^{20}$ |
|---|---|---|---|---|---|---|---|
| 316 | 2-C₆H₅ | O | CH | Cl | OCH₃ | NHCN | |
| 317 | 2-C₆H₅ | O | CH | Cl | OCH₃ | H | |
| 318 | 2-C₆H₅ | O | CH | Cl | OCH₃ | piperidin-1-yl | |
| 319 | 2-C₆H₅ | O | CH | Cl | OCH₃ | morpholin-4-yl | |
| 320 | 2-C₆H₅ | O | CH | Cl | OCH₃ | NH-cyclohexyl | |

TABLE 23

| Comp. No. | X n | W | Z | R¹ | R² | R | Physical nature mp (°C.) $n_D^{20}$ |
|---|---|---|---|---|---|---|---|
| 321 | 2-C₆H₅ | O | CH | Cl | OCH₃ | N(CH₃)(C₆H₅) | |
| 322 | 2-C₆H₅ | O | CH | Cl | OCH₃ | NH-C₆H₄-CH₃ (p) | |
| 323 | 2-C₆H₅ | O | CH | N(CH₃)₂ | OCH₃ | OCH₃ | |
| 324 | 2-C₆H₅ | O | CH | N(CH₃)₂ | OCH₃ | OH | |
| 325 | 2-C₆H₅ | O | CH | N(CH₃)₂ | OCH₃ | OCH₂CH₂Si(CH₃)₃ | |
| 326 | 2-C₆H₅ | O | CH | N(CH₃)₂ | OCH₃ | OCH₃-C₆H₄ | |

TABLE 23-continued

| Comp. No. | X n | W | Z | R¹ | R² | R | Physical nature mp (°C.) $n_D^{20}$ |
|---|---|---|---|---|---|---|---|
| 327 | 2—⌬ | O | CH | N(CH₃)(CH₃) | OCH₃ | OCH₂—⌬—OCH₃ | |
| 328 | 2—⌬ | O | CH | N(CH₃)(CH₃) | OCH₃ | O(CH₂)₂—⌬ | |
| 329 | 2—⌬ | O | CH | N(CH₃)(CH₃) | OCH₃ | OCH₂C₂H₅ | |
| 330 | 2—⌬ | O | CH | N(CH₃)(CH₃) | OCH₃ | ON=C(C₂H₅)(C₂H₅) | |

TABLE 24

| Comp. No. | X n | W | Z | R¹ | R² | R | Physical nature mp (°C.) $n_D^{20}$ |
|---|---|---|---|---|---|---|---|
| 331 | 2—⌬ | O | CH | N(CH₃)(CH₃) | OCH₃ | NHSO₂CH₃ | |
| 332 | 2—⌬ | O | CH | N(CH₃)(CH₃) | OCH₃ | N(CH₃)(SO₂CH₃) | |
| 333 | 2—⌬ | O | CH | N(CH₃)(CH₃) | OCH₃ | N(OC₂H₅)(SO₂CH₃) | |
| 334 | 2—⌬ | O | CH | N(CH₃)(CH₃) | OCH₃ | N(CH₂OCH₃)(SO₂CH₃) | |
| 335 | 2—⌬ | O | CH | N(CH₃)(CH₃) | OCH₃ | N(CH₂COOCH₃)(SO₂CH₃) | |
| 336 | 2—⌬ | O | CH | N(CH₃)(CH₃) | OCH₃ | N(OCH₂CH=CH₂)(SO₂CH₃) | |
| 337 | 2—⌬ | O | CH | N(CH₃)(CH₃) | OCH₃ | N(OCH₂C≡CH)(SO₂CH₃) | |
| 338 | 2—⌬ | O | CH | N(CH₃)(CH₃) | OCH₃ | —N(pyrrolyl) | |

TABLE 24-continued

| Comp. No. | X n | W | Z | R¹ | R² | R | Physical nature mp (°C.) $n_D^{20}$ |
|---|---|---|---|---|---|---|---|
| 339 | 2—⟨phenyl⟩ | O | CH | N(CH₃)(CH₃) | OCH₃ | N(OCH₃)(CH₃) | 10 |

TABLE 25

| Comp. No. | X n | W | Z | R¹ | R² | R | Physical nature mp (°C.) $n_D^{20}$ |
|---|---|---|---|---|---|---|---|
| 340 | 2—⟨phenyl⟩ | O | CH | N(CH₃)(CH₃) | OCH₃ | SC₃H₇ | |
| 341 | 2—⟨phenyl⟩ | O | CH | N(CH₃)(CH₃) | OCH₃ | SCH₂—⟨phenyl⟩—Cl | |
| 342 | 2—⟨phenyl⟩ | O | CH | N(CH₃)(CH₃) | OCH₃ | S—⟨cyclopentyl⟩ | |
| 343 | 2—⟨phenyl⟩ | O | CH | N(CH₃)(CH₃) | OCH₃ | O—⟨cyclohexyl⟩ | |
| 344 | 2—⟨phenyl⟩ | O | CH | N(CH₃)(CH₃) | OCH₃ | O—⟨2,4-dichlorophenyl⟩ | |
| 345 | 2—⟨phenyl⟩ | O | CH | N(CH₃)(CH₃) | OCH₃ | OCH₂COOC₂H₅ | |
| 346 | 2—⟨phenyl⟩ | O | CH | N(CH₃)(CH₃) | OCH₃ | NHOCH₂CH₃ | |
| 347 | 2—⟨phenyl⟩ | O | CH | N(CH₃)(CH₃) | OCH₃ | OC=C (ring) | |
| 348 | 2—⟨phenyl⟩ | O | CH | N(CH₃)(CH₃) | OCH₃ | NHSO₂—⟨phenyl⟩ | |

TABLE 26

| Comp. No. | X | n | W | Z | R¹ | R² | R | Physical nature mp (°C.) $n_D^{20}$ |
|---|---|---|---|---|---|---|---|---|
| 349 | phenyl | 2 | O | CH | N(CH₃)(CH₃) | OCH₃ | N(OCH₃)(SO₂-phenyl) | |
| 350 | phenyl | 2 | O | CH | N(CH₃)(CH₃) | OCH₃ | NHOH | |
| 351 | phenyl | 2 | O | CH | N(CH₃)(CH₃) | OCH₃ | NHOCH₂CH=CH₂ | |
| 352 | phenyl | 2 | O | CH | N(CH₃)(CH₃) | OCH₃ | NHOCH₂C≡CH | |
| 353 | phenyl | 2 | O | CH | N(CH₃)(CH₃) | OCH₃ | NHCH₂CH=CH₂ | |
| 354 | phenyl | 2 | O | CH | N(CH₃)(CH₃) | OCH₃ | NHCH₂C≡CH | |
| 355 | phenyl | 2 | O | CH | N(CH₃)(CH₃) | OCH₃ | NHNH₂ | |
| 356 | phenyl | 2 | O | CH | N(CH₃)(CH₃) | OCH₃ | NHN(CH₃)(CH₃) | |

TABLE 27

| Comp. No. | X | n | W | Z | R¹ | R² | R | Physical nature mp (°C.) $n_D^{20}$ |
|---|---|---|---|---|---|---|---|---|
| 357 | phenyl | 2 | O | CH | N(CH₃)(CH₃) | OCH₃ | NHCOCH₃ | |
| 358 | phenyl | 2 | O | CH | N(CH₃)(CH₃) | OCH₃ | NHCN | |
| 359 | phenyl | 2 | O | CH | N(CH₃)(CH₃) | OCH₃ | H | |
| 360 | phenyl | 2 | O | CH | N(CH₃)(CH₃) | OCH₃ | pyrrolidin-1-yl | |

TABLE 27-continued

| Comp. No. | X n | W | Z | R¹ | R² | R | Physical nature mp (°C.) $n_D^{20}$ |
|---|---|---|---|---|---|---|---|
| 361 | 2-phenyl | O | CH | N(CH₃)CH₃ | OCH₃ | morpholino (N-linked, with O) | |
| 362 | 2-phenyl | O | CH | N(CH₃)CH₃ | OCH₃ | NH-cyclopentyl | |
| 363 | 2-phenyl | O | CH | N(CH₃)CH₃ | OCH₃ | NH-(3,4-dichlorophenyl) | |
| 364 | 2-phenyl | O | CH | N(CH₃)CH₃ | OCH₃ | N(COCH₃)(OCH₂-4-chlorophenyl) | |
| 365 | 2-phenyl | O | CH | OCHF₂ | OCH₃ | OCH₃ | |
| 366 | 2-phenyl | O | CH | OCHF₂ | OCH₃ | OH | |
| 367 | 2-phenyl | O | CH | OCHF₂ | OCH₃ | OCH₂CH₂SI(CH₃)₃ | |
| 368 | 2-phenyl | O | CH | OCHF₂ | OCH₃ | OCH₂-phenyl | |
| 369 | 2-phenyl | O | CH | OCHF₂ | OCH₃ | OCH₂-(4-methoxyphenyl) | |

TABLE 28

| Comp. No. | X n | W | Z | R¹ | R² | R | Physical nature mp (°C.) $n_D^{20}$ |
|---|---|---|---|---|---|---|---|
| 370 | 2-phenyl | O | CH | OCHF₂ | OCH₃ | NHSO₂CH₃ | |
| 371 | 2-phenyl | O | CH | OCHF₂ | OCH₃ | N(CH₂OCH₃)(SO₂CH₃) | |

TABLE 28-continued

| Comp. No. | X | n | W | Z | R¹ | R² | R | Physical nature mp (°C.) $n_D^{20}$ |
|---|---|---|---|---|---|---|---|---|
| 372 | phenyl | 2 | O | CH | OCHF$_2$ | OCH$_3$ | NHCN | |
| 373 | phenyl | 2 | O | CH | OCHF$_2$ | OCH$_3$ | NHOCH$_2$CH=CH$_2$ | |
| 374 | phenyl | 2 | O | CH | OCHF$_2$ | OCH$_3$ | N(SO$_2$CH$_3$)(OCH$_2$CH=CH$_2$) | |
| 375 | phenyl | 2 | O | CH | OCHF$_2$ | OCH$_3$ | NHOCH$_2$COOCH$_3$ | |
| 376 | phenyl | 2 | S | CH | OCH$_3$ | OCH$_3$ | OCH$_3$ | |
| 377 | phenyl | 2 | S | CH | OCH$_3$ | OCH$_3$ | OH | |
| 378 | phenyl | 2 | S | CH | OCH$_3$ | OCH$_3$ | NHSO$_2$CH$_3$ | |
| 379 | phenyl | 2 | S | CH | OCH$_3$ | OCH$_3$ | ON=C(CH$_3$)(CH$_3$) | |
| 380 | phenyl | 2 | S | CH | OCH$_3$ | OCH$_3$ | ONa | |
| 381 | phenyl | 2 | O | N | OCH$_3$ | OCH$_3$ | OC$_2$H$_5$ | |
| 382 | phenyl | 2 | O | N | OCH$_3$ | OCH$_3$ | OH | |
| 383 | phenyl | 2 | O | N | OCH$_3$ | OCH$_3$ | ONa | |

TABLE 29

| Comp. No. | X n | W | Z | R¹ | R² | R | Physical nature mp (°C.) $n_D^{20}$ |
|---|---|---|---|---|---|---|---|
| 384 | 2—⌬ | O | N | OCH₃ | OCH₃ | OH | |
| 385 | 2—⌬ | O | N | OCH₃ | OCH₃ | ONH₃CH(CH₃)₂ | |
| 386 | 2—⌬ | O | N | OCH₃ | OCH₃ | ONH₄ | |
| 387 | 2—⌬ | O | N | OCH₃ | OCH₃ | ONH₂CH(CH₃)₂ | |
| 388 | 2—⌬ | O | N | OCH₃ | OCH₃ | O½Ca | |
| 389 | 2—⌬ | O | N | OCH₃ | OCH₃ | OC=C(CH₃)₂ | |
| 390 | 2—⌬ | O | N | OCH₃ | OCH₃ | OCH₂CH₂N(CH₃)₂ | |
| 391 | 2—⌬ | O | N | OCH₃ | OCH₃ | OCH₂—C₆H₄—OCH₃ | |
| 392 | 2—⌬ | O | N | OCH₃ | OCH₃ | NHSO₂CH₃ | |
| 393 | 2—⌬ | O | N | OCH₃ | OCH₃ | N(CH₂OCH₃)(SO₂CH₃) | |
| 394 | 2—⌬ | O | N | CH₃ | OCH₃ | NHSO₂—C₆H₅ | |
| 395 | 2—⌬ | O | N | CH₃ | OCH₃ | NHSO₂—C₆H₄—Cl | |
| 396 | 2—⌬ | O | N | CH₃ | OCH₃ | —N(imidazolyl) | |
| 397 | 2—⌬ | O | N | CH₃ | OCH₃ | NHOCH₂—C₆H₅ | |

TABLE 30

| Comp. No. | X | n | W | Z | R¹ | R² | R | Physical nature mp (°C.) $n_D^{20}$ |
|---|---|---|---|---|---|---|---|---|
| 398 | phenyl | 2 | O | N | CH₃ | OCH₃ | NHOCH₂-(2-Cl-C₆H₄) | |
| 399 | phenyl | 2 | O | N | NHCH₃ | OCH₃ | OC₃H₇ | |
| 400 | phenyl | 2 | O | N | NHCH₃ | OCH₃ | OH | |
| 401 | phenyl | 2 | O | N | NHCH₃ | NHCH₃ | OC₄H₉ | |
| 402 | phenyl | 2 | O | N | NHCH₃ | NHCH₃ | OH | |
| 403 | phenyl | 2 | O | N | NHCH₃ | NHCH₃ | NHSO₂CH₃ | |
| 404 | pyridyl | 2 | O | CH | OCH₃ | OCH₃ | OCH₂-C₆H₅ | |
| 405 | pyridyl | 2 | O | CH | OCH₃ | OCH₃ | OCH₂-(4-CH₃-C₆H₄) | |
| 406 | pyridyl | 2 | O | CH | OCH₃ | OCH₃ | OCH₂CH₂Si(CH₃)₃ | |

TABLE 30-continued

| Comp. No. | X | n | W | Z | R¹ | R² | R | Physical nature mp (°C.) $n_D^{20}$ |
|---|---|---|---|---|---|---|---|---|
| 407 | 2-pyridyl (N) | 2 | O | CH | OCH$_3$ | OCH$_3$ | OCH$_2$CH=CH$_2$ | |
| 408 | 2-pyridyl (N) | 2 | O | CH | OCH$_3$ | OCH$_3$ | OCH$_2$C≡CH | |
| 409 | 2-pyridyl (N) | 2 | O | CH | OCH$_3$ | OCH$_3$ | SC$_2$H$_5$ | |
| 410 | 2-pyridyl (N) | 2 | O | CH | OCH$_3$ | OCH$_3$ | SCH$_2$-phenyl | |
| 411 | 2-pyridyl (N) | 2 | O | CH | OCH$_3$ | OCH$_3$ | O-phenyl | |

TABLE 31

| Comp. No. | X n | W | Z | R¹ | R² | R | Physical nature mp (°C.) $n_D^{20}$ |
|---|---|---|---|---|---|---|---|
| 412 | 2-pyridyl | O | CH | OCH₃ | OCH₃ | 2-methylphenoxy (o-CH₃-C₆H₄-O) | |
| 413 | 2-pyridyl | O | CH | OCH₃ | OCH₃ | (2-chlorophenyl)methoxy (o-Cl-C₆H₄-OCH₂) | |
| 414 | 2-pyridyl | O | CH | OCH₃ | OCH₃ | OCH₂OCH₃ | |
| 415 | 2-pyridyl | O | CH | OCH₃ | OCH₃ | OCH₂CN | |
| 416 | 2-pyridyl | O | CH | OCH₃ | OCH₃ | OCH₂COOCH₃ | |
| 417 | 2-pyridyl | O | CH | OCH₃ | OCH₃ | cyclohexylidene-aminoxy (ON=C(CH₂)₅) | |
| 418 | 2-pyridyl | O | CH | OCH₃ | OCH₃ | NHSO₂C₂H₅ | |
| 419 | 2-pyridyl | O | CH | OCH₃ | OCH₃ | NHSO₂-C₆H₅ | |
| 420 | 2-pyridyl | O | CH | OCH₃ | OCH₃ | 2-nitrophenylsulfonamido (o-NO₂-C₆H₄-NHSO₂) | |
| 421 | 2-pyridyl | O | CH | OCH₃ | OCH₃ | NH₂ | |
| 422 | 2-pyridyl | O | CH | OCH₃ | OCH₃ | NHOH | |
| 423 | 2-pyridyl | O | CH | OCH₃ | OCH₃ | NHOCH₃ | |
| 424 | 2-pyridyl | O | CH | OCH₃ | OCH₃ | N(OCH₃)(CH₃) | |

TABLE 31-continued

| Comp. No. | X | n | W | Z | R¹ | R² | R | Physical nature mp (°C.) $n_D^{20}$ |
|---|---|---|---|---|---|---|---|---|
| 425 | 2-pyridyl (N at position adjacent) | 2 | O | CH | OCH$_3$ | OCH$_3$ | NHOCH$_2$CH=CH$_2$ | |

TABLE 32

| Comp. No. | X | n | W | Z | R¹ | R² | R | Physical nature mp (°C.) $n_D^{20}$ |
|---|---|---|---|---|---|---|---|---|
| 426 | 2-pyridyl | 2 | O | CH | OCH$_3$ | OCH$_3$ | N(OCH$_2$CH=CH$_2$)(SO$_2$CH$_3$) | |
| 427 | 2-pyridyl | 2 | O | CH | OCH$_3$ | OCH$_3$ | N(OCH$_3$)(SO$_2$C$_6$H$_5$) | |
| 428 | 2-pyridyl | 2 | O | CH | OCH$_3$ | OCH$_3$ | NHOCH$_2$COOCH$_3$ | |
| 429 | 2-pyridyl | 2 | O | CH | OCH$_3$ | OCH$_3$ | N(OCH$_2$COOCH$_3$)(SO$_2$CH$_3$) | |
| 430 | 4-pyridyl | 2 | O | CH | OCH$_3$ | OCH$_3$ | OCH$_2$-(4-CH$_3$-C$_6$H$_4$) | |
| 431 | 4-pyridyl | 2 | O | CH | OCH$_3$ | OCH$_3$ | OCH$_2$CH$_2$Si(CH$_3$)$_3$ | |
| 432 | 4-pyridyl | 2 | O | CH | OCH$_3$ | OCH$_3$ | OCH$_2$CH=CH$_2$ | |
| 433 | 4-pyridyl | 2 | O | CH | OCH$_3$ | OCH$_3$ | N(CH$_3$OCH$_3$)(SO$_2$CH$_3$) | |
| 434 | 4-pyridyl | 2 | O | CH | OCH$_3$ | OCH$_3$ | N(OC$_2$H$_5$)(SO$_2$CH$_3$) | |
| 435 | 4-pyridyl | 2 | O | CH | OCH$_3$ | OCH$_3$ | OCH$_2$OCH$_3$ | |
| 436 | 4-pyridyl | 2 | O | CH | OCH$_3$ | OCH$_3$ | OCH$_2$CH$_2$N(CH$_3$)$_2$ | |

TABLE 33

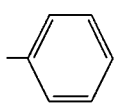

| Comp. No. | X n | W | Z | R¹ | R² | R³ | R | Physical nature mp (°C.) $n_D^{20}$ |
|---|---|---|---|---|---|---|---|---|
| 437 | 5-$CH_3$ | O | CH | $OCH_3$ | $OCH_3$ | H | OH | 157–159 |
| 438 | 5-$CH_3$ | O | CH | $OCH_3$ | $OCH_3$ | N | $OC_2H_5$ | 159–161 |
| 439 | 4-$COOC_2H_5$ | O | CH | $OCH_3$ | $OCH_3$ | $CH_3$ | $OC_2H_5$ | 103–104 |
| 440 | 4-$COOC_2H_5$ | O | CH | $OCH_3$ | $OCH_3$ | H | $OC_2H_5$ | 159–161 |
| 441 | H | O | N | $OCH_3$ | $OCH_3$ | $CH_3$ | $OCH_3$ | |
| 442 | H | O | N | $OCH_3$ | $OCH_3$ | $CH_3$ | OH | |
| 443 | H | S | CH | $OCH_3$ | $OCH_3$ | $CH_3$ | $OCH_3$ | |
| 444 | H | S | CH | $OCH_3$ | $OCH_3$ | $CH_3$ | OH | |
| 445 | H | S | CH | $OCH_3$ | $OCH_3$ | –C₆H₅ (benzyl) | OH | |
| 446 | H | S | CH | $OCH_3$ | $OCH_3$ | –C₆H₅ (benzyl) | $OCH_3$ | |
| 447 | H | O | CH | Cl | $OCH_3$ | –CH₂–C₆H₄–CH₃ | OH | |
| 448 | H | O | CH | Cl | $OCH_3$ | –CH₂–C₆H₄–CH₃ | $OC_2H_5$ | |
| 449 | H | NH | CH | $OCH_3$ | $OCH_3$ | –CH₂–C₆H₄–Cl | OH | |
| 450 | H | N–H | CH | $OCH_3$ | $OCH_3$ | –CH₂–C₆H₄–Cl | $OCH_3$ | |
| 451 | H | N–CHO | CH | $OCH_3$ | $OCH_3$ | –CH₂–C₆H₄–Cl | $OCH_3$ | |

TABLE 34

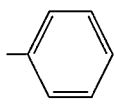

| Comp. No. | X | W | Z | R¹ | R² | R | Physical nature mp (°C.) $n_D^{20}$ |
|---|---|---|---|---|---|---|---|
| 452 | $CH_3$ | O | CH | $OCH_3$ | $OCH_3$ | OH | 155–158 |

TABLE 34-continued

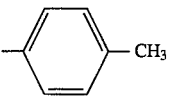

| Comp. No. | X | W | Z | R¹ | R² | R | Physical nature mp (°C.) $n_D^{20}$ |
|---|---|---|---|---|---|---|---|
| 453 | $CH_3$ | O | CH | $OCH_3$ | $OCH_3$ | $OC_2H_5$ | 1.5133 |

TABLE 34-continued

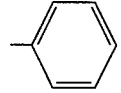

| Comp. No. | X | W | Z | R¹ | R² | R | Physical nature mp (°C.) $n_D^{20}$ |
|---|---|---|---|---|---|---|---|
| 454 | CH₃ | O | N | OCH₃ | OCH₃ | OH | |
| 455 | CH₃ | O | N | OCH₃ | OCH₃ | OCH₃ | |
| 456 | CH₃ | O | CH | Cl | OCH₃ | OH | |

TABLE 34-continued

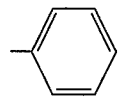

| Comp. No. | X | W | Z | R¹ | R² | R | Physical nature mp (°C.) $n_D^{20}$ |
|---|---|---|---|---|---|---|---|
| 457 | CH₃ | O | CH | Cl | OCH₃ | OC₂H₅ | |

TABLE 35

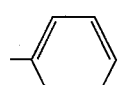

| Comp. No. | X n | W | Z | R¹ | R² | R | Physical nature mp (°C.) $n_D^{20}$ |
|---|---|---|---|---|---|---|---|
| 458 | CH₃ | NH | CH | OCH₃ | OCH₃ | OCH₃ | 175–176 |
| 459 | CH₃ | NH | CH | OCH₃ | OCH₃ | OH | 219–222 |
| 460 | CH₃ | N—CH₃ | CH | OCH₃ | OCH₃ | OH | 147–149 |
| 461 | 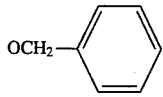 | NH | CH | OCH₃ | OCH₃ | OCH₃ | 152–154.5 |
| 462 | 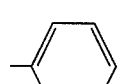 | NH | CH | OCH₃ | OCH₃ | OH | 200–204 |
| 463 | 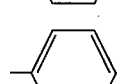 | N—CHO | CH | OCH₃ | OCH₃ | OCH₂—phenyl | |
| 464 | 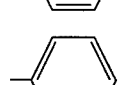 | N—CHO | CH | OCH₃ | OCH₃ | OH | |
| 465 |  | S | CH | OCH₃ | OCH₃ | OH | |
| 466 | 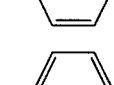 | S | CH | OCH₃ | OCH₃ | OCH₃ | |
| 467 | | S | CH | Cl | OCH₃ | OH | |
| 468 | | S | CH | Cl | OCH₃ | OCH₃ | |

TABLE 35-continued

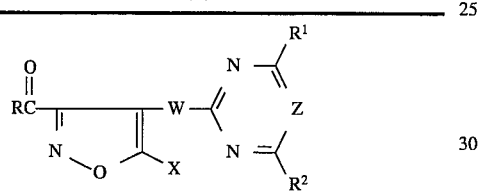

| Comp. No. | X n | W | Z | R¹ | R² | R | Physical nature mp (°C.) $n_D^{20}$ |
|---|---|---|---|---|---|---|---|
| 469 | phenyl | S | CH | $CH_3$ | $CH_3$ | OH | |
| 470 | phenyl | S | CH | $CH_3$ | $CH_3$ | $OCH_3$ | |

TABLE 36

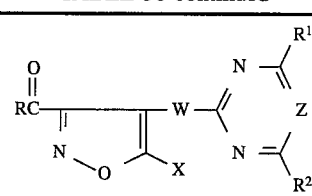

| Comp. No. | X | W | Z | R¹ | R² | R | Physical nature mp (°C.) $n_D^{20}$ |
|---|---|---|---|---|---|---|---|
| 471 | H | O | CH | $OCH_3$ | $OCH_3$ | OH | 159–160 |
| 472 | H | O | CH | $OCH_3$ | $OCH_3$ | $OC_2H_5$ | 81–83 |
| 473 | H | S | CH | $OCH_3$ | $OCH_3$ | OH | |
| 474 | H | S | CH | $OCH_3$ | $OCH_3$ | $OCH_3$ | |
| 475 | H | NH | CH | $OCH_3$ | $OCH_3$ | OH | |
| 476 | H | N—CHO | CH | $OCH_3$ | $OCH_3$ | $OCH_3$ | |

TABLE 36-continued

| Comp. No. | X | W | Z | R¹ | R² | R | Physical nature mp (°C.) $n_D^{20}$ |
|---|---|---|---|---|---|---|---|
| 477 | H | O | CH | Cl | $OCH_3$ | OH | |
| 478 | H | O | CH | Cl | $OCH_3$ | $OC_2H_5$ | |
| 479 | H | O | CH | $OCH_3$ | $OCH_3$ | O½Cu | 148–152 |

TABLE 37

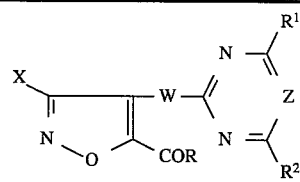

| Comp. No. | X | W | Z | R¹ | R² | R | Physical nature mp (°C.) $n_D^{20}$ |
|---|---|---|---|---|---|---|---|
| 480 | $CH_3$ | O | CH | $OCH_3$ | $OCH_3$ | OH | 139–141 |
| 481 | $CH_3$ | O | CH | $OCH_3$ | $OCH_3$ | $OC_2H_5$ | 63–66 |
| 482 | $CH_3$ | O | CH | $OCH_3$ | $OCH_3$ | $OC_4H_9$ | |
| 483 | $CH_3$ | O | CH | Cl | $OCH_3$ | $OC_3H_7$ | |
| 484 | $CH_3$ | O | CH | Cl | $OCH_3$ | OH | |
| 485 | $CH_3$ | O | CH | $OCHF_2$ | $OCH_3$ | $OCH_3$ | |
| 486 | $CH_3$ | O | CH | $OCHF_2$ | $OCH_3$ | OH | |
| 487 | $CH_3$ | O | CH | $OCH_3$ | $OCH_3$ | ON=C(CH₃)₂ | |
| 488 | $CH_3$ | O | CH | $OCH_3$ | $OCH_3$ | $NHSO_2CH_3$ | 145–148 |

TABLE 37-continued
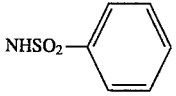
| Comp. No. | X | W | Z | R¹ | R² | R | Physical nature mp (°C.) $n_D^{20}$ |
|---|---|---|---|---|---|---|---|
| 489 | $CH_3$ | O | CH | $OCH_3$ | $OCH_3$ | $NHSO_2C_3H_7$ | |
| 490 | $CH_3$ | O | CH | $OCH_3$ | $OCH_3$ | 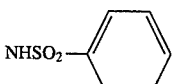 | |
| 491 | $CH_3$ | O | CH | $OCH_3$ | $OCH_3$ | 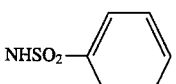 | |
| 492 | $CH_3$ | O | CH | $OCH_3$ | $OCH_3$ | 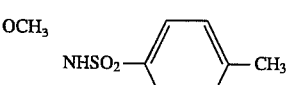 | |
| 493 | $CH_3$ | O | CH | $OCH_3$ | $OCH_3$ | 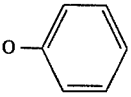 | |
TABLE 38
| Comp. No. | X | W | Z | R¹ | R² | R | Physical nature mp (°C.) $n_D^{20}$ |
|---|---|---|---|---|---|---|---|
| 494 | $CH_3$ | O | CH | $OCH_3$ | $OCH_3$ | 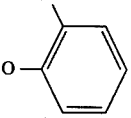 | |
| 495 | $CH_3$ | O | CH | $OCH_3$ | $OCH_3$ | 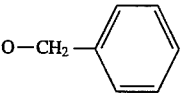 | |
| 496 | $CH_3$ | O | CH | $OCH_3$ | $OCH_3$ | 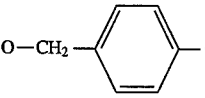 | |
| 497 | $CH_3$ | O | CH | $OCH_3$ | $OCH_3$ | $O-CH_2-\phi-Cl$ | |

TABLE 39

(structure with X, COR, R¹, R², W, Z, N, S)

| Comp. No. | X | W | Z | R¹ | R² | R | Physical nature mp (°C.) $n_D^{20}$ |
|---|---|---|---|---|---|---|---|
| 498 | CH₃ | N—CH₃ | CH | OCH₃ | OCH₃ | OH | 146–149 |
| 499 | CH₃ | N—CH₃ | CH | OCH₃ | OCH₃ | OC₂H₅ | 96–100 |
| 500 | CH₃ | N—CH₃ | CH | Cl | OCH₃ | OCH₃ | |
| 501 | CH₃ | N—CH₃ | CH | Cl | OCH₃ | OH | |
| 502 | CH₃ | N—CH₃ | CH | OCHF₂ | OCH₃ | OCH₃ | |
| 503 | CH₃ | N—CH₃ | CH | OCHF₂ | OCH₃ | OH | |
| 504 | CH₃ | N—CH₃ | CH | N(CH₃)₂ | OCH₃ | OC₂H₅ | |
| 505 | CH₃ | N—CH₃ | CH | N(CH₃)₂ | OCH₃ | OH | |
| 506 | CH₃ | N—CH₃ | N | OCH₃ | OCH₃ | OC₃H₇ | |
| 507 | CH₃ | N—CH₃ | N | OCH₃ | OCH₃ | OCH₂—C₆H₅ | |
| 508 | CH₃ | N—CH₃ | N | OCH₃ | OCH₃ | OH | |

TABLE 40

(structure with X, N, O, COR, W, Z, R¹, R²)

| Comp. No. | X | W | Z | R¹ | R² | R | Physical nature mp (°C.) $n_D^{20}$ |
|---|---|---|---|---|---|---|---|
| 509 | CH₃ | O | CH | OCH₃ | OCH₃ | OC₂H₅ | |
| 510 | CH₃ | O | CH | OCH₃ | OCH₃ | OH | |
| 511 | CH₃ | O | CH | OCH₃ | OCH₃ | OCH₂—C₆H₅ | |
| 512 | CH₃ | O | CH | Cl | OCH₃ | OCH₃ | |
| 513 | CH₃ | O | CH | Cl | OCH₃ | OH | |
| 514 | CH₃ | O | CH | N(CH₃)₂ | OCH₃ | OC₂H₅ | |

TABLE 40-continued
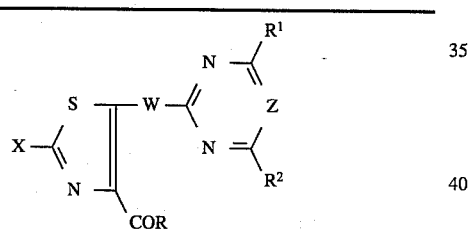
| Comp. No. | X | W | Z | R¹ | R² | R | Physical nature mp (°C.) $n_D^{20}$ |
|---|---|---|---|---|---|---|---|
| 515 | CH₃ | O | CH | N(CH₃)(CH₃) | OCH₃ | OH | |
| 516 | 2-Cl-phenyl | O | CH | OCH₃ | OCH₃ | OCH₃ | |
| 517 | 2-Cl-phenyl | O | CH | OCH₃ | OCH₃ | OH | |
TABLE 41
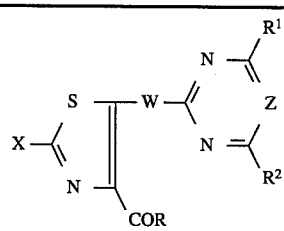
| Comp. No. | X | W | Z | R¹ | R² | R | Physical nature mp (°C.) $n_D^{20}$ |
|---|---|---|---|---|---|---|---|
| 518 | H | S | CH | OCH₃ | OCH₃ | OCH₃ | 233–239 |
| 519 | H | S | CH | OCH₃ | OCH₃ | OC₂H₅ | |
| 520 | H | S | CH | Cl | OCH₃ | OCH₃ | |
| 521 | H | S | CH | CH₃ | CH₃ | OCH₃ | |
| 522 | H | S | N | OCH₃ | OCH₃ | OC₂H₅ | |

TABLE 42

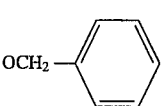

| Comp. No. | X | W | Z | R¹ | R² | R | Physical nature mp (°C.) $n_D^{20}$ |
|---|---|---|---|---|---|---|---|
| 523 | CH₃ | O | N | OCH₃ | OCH₃ | OC₂H₅ | 93–94 |
| 524 | CH₃ | O | N | OCH₃ | OCH₃ | OH | |
| 525 | CH₃ | O | N | OCH₃ | OCH₃ | 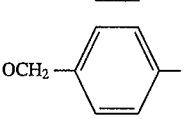 | |
| 526 | CH₃ | O | N | OCH₃ | OCH₃ | 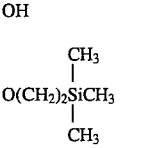 | |
| 527 | CH₃ | O | CH | OCH₃ | OCH₃ | OC₃H₇ | |
| 528 | CH₃ | O | CH | OCH₃ | OCH₃ | OH | |
| 529 | CH₂S | S | N | OCH₃ | OCH₃ | OC₂H₅ | 121–123 |
| 530 | CH₂S | S | N | OCH₃ | OCH₃ | OH | |
| 531 | CH₂S | S | N | OCH₃ | OCH₃ | 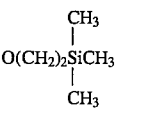 | |
| 532 | CH₂S | S | N | OCH₃ | OCH₃ | OCH₃ | |
| 533 | CH₂S | S | CH | OCH₃ | OCH₃ | OC₂H₅ | 95–98 |
| 534 | CH₂S | S | CH | OCH₃ | OCH₃ | 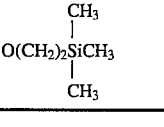 | |
| 535 | CH₂S | S | CH | OCH₃ | OCH₃ | O(CH₂)₂Si(CH₃)₃ | |

Note: entries 531 and 534 R group = O(CH₂)₂Si(CH₃)₃ (with three CH₃ on Si shown as CH₃/CH₃/CH₃).

TABLE 43
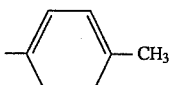
| Comp. No. | X | W | Z | R¹ | R² | R³ | R | Physical nature mp (°C.) $n_D^{20}$ |
|---|---|---|---|---|---|---|---|---|
| 536 | $CH_3S$ | O | CH | $OCH_3$ | $OCH_3$ | -C₆H₄-CH₃ | OH | 154–157 |
| 537 | $CH_3S$ | O | CH | $OCH_3$ | $OCH_3$ | -C₆H₄-CH₃ | $OC_2H_5$ | 147–148 |
| 538 | $CH_3S$ | O | CH | $OCH_3$ | $OCH_3$ | -C₆H₄-CH₃ | $OCH_2C_6H_5$ | |
| 539 | $CH_3S$ | O | CH | Cl | $OCH_3$ | -C₆H₄-CH₃ | $OCH_3$ | |
| 540 | $CH_3S$ | O | CH | Cl | $OCH_3$ | -C₆H₄-CH₃ | OH | |
| 541 | $CH_3S$ | O | CH | $OCH_3$ | $OCH_3$ | -C₆H₄-CH₃ | ONa | |
| 542 | $CH_3S$ | O | CH | $OCH_3$ | $OCH_3$ | -C₆H₄-CH₃ | O½Ca | |
| 543 | $CH_3S$ | O | CH | $OCH_3$ | $OCH_3$ | -C₆H₄-CH₃ | $OH_2N(C_2H_5)(C_5H_5)$ | |

TABLE 44
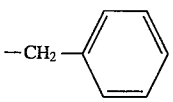
| Comp. No. | W | Z | R[1] | R[2] | R[3] | R | Physical nature mp (°C.) $n_D^{20}$ |
|---|---|---|---|---|---|---|---|
| 544 | O | CH | OCH₃ | OCH₃ | CH₃ | OH | |
| 545 | O | CH | OCH₃ | OCH₃ | CH₃ | OCH₃ | |
| 546 | O | CH | OCH₃ | OCH₃ | H | OH | |
| 547 | O | CH | OCH₃ | OCH₃ | H | OC₂H₅ | |
| 548 | O | CH | OCH₃ | OCH₃ | —CH₂—C₆H₅ | H | |
| 549 | O | CH | OCH₃ | OCH₃ | —CH₂—C₆H₅ | OH | |
| 550 | S | CH | OCH₃ | OCH₃ | C₆H₅ | H | |
| 551 | S | CH | OCH₃ | OCH₃ | C₆H₅ | OH | |
| 552 | O | CH | OCH₃ | OCH₃ | CH₂—C₆H₄—Cl | H | |
| 553 | O | CH | OCH₃ | OCH₃ | CH₂—C₆H₄—Cl | OH | |
| 554 | S | CH | OCH₃ | OCH₃ | CH₂—C₆H₄—OCH₃ | H | |
| 555 | S | CH | OCH₃ | OCH₃ | CH₂—C₆H₄—OCH₃ | OH | |

TABLE 45

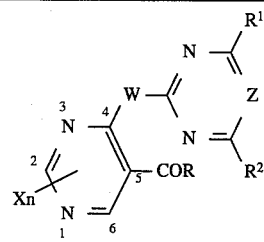

| Comp. No. | Xn | W | Z | R¹ | R² | R | Physical nature mp (°C.) $n_D^{20}$ |
|---|---|---|---|---|---|---|---|
| 556 | H | O | CH | OCH₃ | OCH₃ | OC₂H₅ | 1.5389 |
| 557 | H | O | CH | OCH₃ | OCH₃ | OH | |
| 558 | H | S | CH | OCH₃ | OCH₃ | OCH₃ | |
| 559 | H | S | CH | OCH₃ | OCH₃ | OH | |
| 560 | H | NH | CH | OCH₃ | OCH₃ | OC₂H₅ | |
| 561 | H | NH | CH | OCH₃ | OCH₃ | OH | |
| 562 | 2-C₆H₅ | O | CH | OCH₃ | OCH₃ | OC₂H₅ | 105–108 |
| 563 | 2-C₆H₅ | O | CH | OCH₃ | OCH₃ | OH | |
| 564 | 2-C₆H₅ | S | CH | OCH₃ | OCH₃ | OC₂H₅ | 135–137 |
| 565 | 2-C₆H₅ | S | CH | OCH₃ | OCH₃ | OH | 185–187 |
| 566 | 2-C₆H₅ | S | N | OCH₃ | OCH₃ | OC₂H₅ | |
| 567 | 6-C₆H₅ | O | CH | OCH₃ | OCH₃ | OCH₃ | |
| 568 | 6-C₆H₅ | O | CH | OCH₃ | OCH₃ | OH | |
| 569 | H | O | CH | Cl | OCH₃ | OH | |

TABLE 46

| Comp. No. | Xn | W | Z | R¹ | R² | R | Physical nature mp (°C.) $n_D^{20}$ |
|---|---|---|---|---|---|---|---|
| 570 | H | O | CH | Cl | OCH₃ | OC₂H₅ | |
| 571 | H | O | CH | CH₃ | OCH₃ | OC₂H₅ | |
| 572 | H | O | CH | OCHF₂ | OCH₃ | OC₂H₅ | |
| 573 | H | O | CH | OCHF₂ | OCH₃ | OH | |
| 574 | 2-CH₃ | O | CH | OCH₃ | OCH₃ | OC₂H₅ | |

TABLE 46-continued

| Comp. No. | Xn | W | Z | R¹ | R² | R | Physical nature mp (°C.) $n_D^{20}$ |
|---|---|---|---|---|---|---|---|
| 575 | 2-CH₃ | O | CH | OCH₃ | OCH₃ | OH | |
| 576 | 2-CH₃ | O | CH | Cl | OCH₃ | OCH₃ | |
| 577 | 2-CH₃ | O | CH | Cl | OCH₃ | OH | |
| 578 | 6-S-[4,6-dimethoxypyrimidin-2-yl] | S | CH | OCH3 | OCH₃ | OCH₃ | |
| 579 | 6-S-[4,6-dimethoxypyrimidin-2-yl] | S | CH | OCH₃ | OCH₃ | OH | |
| 580 | 6-O-[4,6-dimethoxypyrimidin-2-yl] | O | CH | OCH₃ | OCH₃ | OC₂H₅ | |
| 581 | 6-O-[4,6-dimethoxypyrimidin-2-yl] | O | CH | OCH₃ | OCH₃ | OH | |
| 582 | 6-Cl | O | CH | OCH₃ | OCH₃ | OCH₃ | |
| 583 | 6-Cl | O | CH | OCH₃ | OCH₃ | OH | |
| 584 | 6-Cl | O | N | OCH₃ | OCH₃ | OCH₃ | |
| 585 | 6-Cl | O | N | OCH₃ | OCH₃ | OH | |
| 586 | 6-Cl | S | CH | OCH₃ | OCH₃ | OCH₃ | |
| 587 | 6-Cl | S | CH | OCH₃ | OCH₃ | OH | |
| 588 | 6-Cl | S | N | OCH₃ | OCH₃ | OCH₃ | |
| 589 | 6-Cl | S | N | OCH₃ | OCH₃ | OH | |

TABLE 47

| Comp. No. | Xn | W | Z | R¹ | R² | R | Physical nature mp (°C.) $n_D^{20}$ |
|---|---|---|---|---|---|---|---|
| 590 | 6-OC₂H₅ | O | CH | OCH₃ | OCH₃ | OCH₃ | |
| 591 | 6-OC₂H₅ | O | CH | OCH₃ | OCH₃ | OH | |
| 592 | 6-OC₂H₅ | O | N | OCH₃ | OCH₃ | OCH₃ | |
| 593 | 6-OC₂H₅ | O | N | OCH₃ | OCH₃ | OH | |
| 594 | 6-OC₂H₅ | S | CH | OCH₃ | OCH₃ | OCH₃ | |
| 595 | 6-OC₂H₅ | S | CH | OCH₃ | OCH₃ | OH | |
| 596 | 6-O-phenyl | O | CH | OCH₃ | OCH₃ | OCH₃ | |

TABLE 47-continued

| Comp. No. | Xn | W | Z | R¹ | R² | R | Physical nature mp (°C.) $n_D^{20}$ |
|---|---|---|---|---|---|---|---|
| 597 | 6-O-C₆H₅ | O | CH | OCH₃ | OCH₃ | OH | |
| 598 | 6-O-(2-CH₃)C₆H₄ | O | CH | OCH₃ | OCH₃ | OCH₃ | |
| 599 | 6-O-(2-CH₃)C₆H₄ | O | CH | OCH₃ | OCH₃ | OH | |
| 600 | 6-O-(4-Cl)C₆H₄ | O | CH | OCH₃ | OCH₃ | OCH₃ | |
| 601 | 6-O-(4-Cl)C₆H₄ | O | CH | OCH₃ | OCH₃ | OH | |
| 602 | 6-NHCH(CH₃)₂ | O | CH | OCH₃ | OCH₃ | OCH₃ | |
| 603 | 6-NHCH(CH₃)₂ | O | CH | OCH₃ | OCH₃ | OH | |
| 604 | 6-N(C₂H₅)₂ | O | CH | OCH₃ | OCH₃ | OCH₃ | |
| 605 | 6-N(C₂H₅)₂ | O | CH | OCH₃ | OCH₃ | OH | |
| 606 | 6-SCH₃ | O | CH | OCH₃ | OCH₃ | OCH₃ | |
| 607 | 6-SCH₃ | O | CH | OCH₃ | OCH₃ | OH | |

TABLE 48

| Comp. No. | Xn | W | Z | R¹ | R² | R | Physical nature mp (°C.) $n_D^{20}$ |
|---|---|---|---|---|---|---|---|
| 608 | 6-S-C₆H₅ | O | CH | OCH₃ | OCH₃ | OCH₃ | |
| 609 | 6-S-C₆H₅ | O | CH | OCH₃ | OCH₃ | OH | |
| 610 | 6-SO₂CH₃ | O | CH | OCH₃ | OCH₃ | OCH₃ | |
| 611 | 6-SO₂CH₃ | O | CH | OCH₃ | OCH₃ | OH | |

TABLE 48-continued

| Comp. No. | Xn | W | Z | R¹ | R² | R | Physical nature mp (°C.) $n_D^{20}$ |
|---|---|---|---|---|---|---|---|
| 612 | 6-NH—C₆H₄(CH₃) | O | CH | OCH₃ | OCH₃ | OCH₃ | |
| 613 | 6-NH—C₆H₄(CH₃) | O | CH | OCH₃ | OCH₃ | OH | |
| 614 | 6-C₆H₅ | O | CH | OCH₃ | OCH₃ | OCH₃ | |
| 615 | 6-C₆H₅ | O | CH | OCH₃ | OCH₃ | OH | |
| 616 | 6-C₆H₅ | NH | CH | OCH₃ | OCH₃ | OCH₃ | |
| 617 | 6-C₆H₅ | NH | CH | OCH₃ | OCH₃ | OH | |
| 618 | 6-OCH₂CH(CH₃)₂ | O | N | OCH₃ | OCH₃ | OCH₃ | |
| 619 | 6-OCH₂CH(CH₃)₂ | O | N | OCH₃ | OCH₃ | OH | |
| 620 | 6-OCH(CH₃)₂ | O | CH | Cl | OCH₃ | OCH₃ | |
| 621 | 6-OCH(CH₃)₂ | O | CH | Cl | OCH₃ | OH | |

TABLE 49

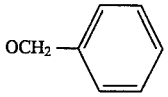

| Comp. No. | Xn | W | Z | R[1] | R[2] | R | Physical nature mp (°C.) $n_D^{20}$ |
|---|---|---|---|---|---|---|---|
| 622 | H | O | CH | OCH₃ | OCH₃ | OCH₃ | 88–93 |
| 623 | H | O | CH | OCH₃ | OCH₃ | OH | |
| 624 | H | S | CH | OCH₃ | OCH₃ | OCH₂—C₆H₅ | 115–117 |
| 625 | H | S | CH | OCH₃ | OCH₃ | OH | 136–138 |
| 626 | H | S | N | OCH₃ | OCH₃ | OC₂H₅ | |
| 627 | H | S | N | OCH₃ | OCH₃ | OH | |
| 628 | H | O | CH | Cl | OCH₃ | OCH₃ | |
| 629 | H | O | CH | Cl | OCH₃ | OH | |
| 630 | H | O | CH | OCHF₂ | OCH₃ | OC₃H₇ | |
| 631 | H | O | CH | OCHF₂ | OCH₃ | OH | |
| 632 | H | O | N | CH₃ | OCH₃ | OC₂H₅ | |
| 633 | H | O | N | CH₃ | OCH₃ | OH | 30 |

TABLE 50

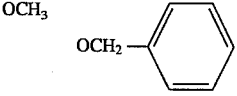

| Comp. No. | Xn | W | Z | R[1] | R[2] | R | Physical nature mp (°C.) $n_D^{20}$ |
|---|---|---|---|---|---|---|---|
| 634 | H | NH | CH | OCH₃ | OCH₃ | OC₂H₅ | |
| 635 | H | NH | CH | OCH₃ | OCH₃ | OH | |
| 636 | H | N—CHO | CH | OCH₃ | OCH₃ | OCH₃ | |
| 637 | H | N—CHO | CH | OCH₃ | OCH₃ | OCH₂—C₆H₅ | |
| 638 | H | N—CHO | CH | OCH₃ | OCH₃ | OH | |
| 639 | H | NH | N | OCH₃ | OCH₃ | OH | |
| 640 | H | NH | N | OCH₃ | OCH₃ | OC₂H₅ | |
| 641 | H | N—CH₃ | N | OCH₃ | OCH₃ | OCH₃ | |
| 642 | H | N—CH₃ | N | OCH₃ | OCH₃ | OH | |
| 643 | H | N—CHO | N | OCH₃ | OCH₃ | OCH₃ | |
| 644 | H | N—CH₃ | N | CH₃ | OCH₃ | OC₂H₅ | |
| 645 | H | N—CH₃ | N | CH₃ | OCH₃ | OH | |

TABLE 51

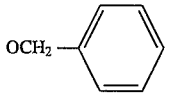

| Comp. No. | Xn | W | Z | R¹ | R² | R | Physical nature mp (°C.) $n_D^{20}$ |
|---|---|---|---|---|---|---|---|
| 646 | H | NH | CH | OCH$_3$ | OCH$_3$ | OC$_2$H$_5$ | |
| 647 | H | NH | CH | OCH$_3$ | OCH$_3$ | OH | |
| 648 | H | N—CHO | CH | OCH$_3$ | OCH$_3$ | OCH$_3$ | |
| 649 | H | N—CHO | CH | OCH$_3$ | OCH$_3$ | OCH$_2$—C$_6$H$_5$ | |
| 650 | H | N—CHO | CH | OCH$_3$ | OCH$_3$ | OH | |
| 651 | H | NH | N | OCH$_3$ | OCH$_3$ | OH | |
| 652 | H | NH | N | OCH$_3$ | OCH$_3$ | OC$_2$H$_5$ | |
| 653 | H | N—CH$_3$ | N | OCH$_3$ | OCH$_3$ | OCH$_3$ | |
| 654 | H | N—CH$_3$ | N | OCH$_3$ | OCH$_3$ | OH | |
| 655 | H | N—CHO | N | OCH$_3$ | OCH$_3$ | OCH$_3$ | |
| 656 | H | N—CH$_3$ | N | CH$_3$ | OCH$_3$ | OC$_2$H$_5$ | |
| 657 | H | N—CH$_3$ | N | CH$_3$ | OCH$_3$ | OH | |
| 658 | 3—C$_6$H$_5$, 6—C$_6$H$_5$ | O | CH | OCH$_3$ | OCH$_3$ | OCH$_3$ | |
| 659 | 3—C$_6$H$_5$, 6—C$_6$H$_5$ | O | CH | OCH$_3$ | OCH$_3$ | OH | |

TABLE 52

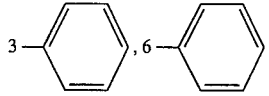

| Comp. No. | X | W | Z | R¹ | R² | R | Physical nature mp (°C.) $n_D^{20}$ |
|---|---|---|---|---|---|---|---|
| 660 | CH$_3$S | O | CH | OCH$_3$ | OCH$_3$ | OC$_2$H$_5$ | 1.5628 |
| 661 | CH$_3$S | O | CH | OCH$_3$ | OCH$_3$ | OH | |
| 662 | CH$_3$S | O | CH | Cl | OCH$_3$ | OCH$_3$ | |
| 663 | CH$_3$S | O | CH | Cl | OCH$_3$ | OH | |
| 664 | CH$_3$S | O | CH | OCHF$_2$ | OCH$_3$ | OCH$_3$ | |
| 665 | CH$_3$S | O | CH | OCHF$_2$ | OCH$_3$ | OH | |
| 666 | CH$_3$ | O | CH | OCH$_3$ | OCH$_3$ | OC$_3$H$_7$ | |

TABLE 52-continued

| Comp. No. | X | W | Z | R¹ | R² | R | Physical nature mp (°C.) $n_D^{20}$ |
|---|---|---|---|---|---|---|---|
| 667 | CH₃ | O | CH | OCH₃ | OCH₃ | OCH₂—C₆H₅ | |
| 668 | CH₃ | O | CH | OCH₃ | OCH₃ | OH | |
| 669 | CH₃ | O | CH | Cl | OCH₃ | OC₄H₅ | |
| 670 | CH₃ | O | CH | Cl | OCH₃ | OCH(CH₃)₂ | |
| 671 | CH₃ | O | CH | Cl | OCH₃ | OH | |
| 672 | CH₃ | O | CH | N(CH₃)₂ | OCH₃ | O—C₃H₇ | |
| 673 | CH₃ | O | CH | N(CH₃)₂ | OCH₃ | OH | |

TABLE 53

| Comp. No. | Xn | W | Z | R¹ | R² | R | Physical nature mp (°C.) $n_D^{20}$ |
|---|---|---|---|---|---|---|---|
| 674 | H | O | CH | OCH₃ | OCH₃ | OCH₃ | 135–138 |
| 675 | H | O | CH | OCH₃ | OCH₃ | OH | 154–159 |
| 676 | H | O | CH | Cl | OCH₃ | OC₂H₅ | |
| 677 | H | O | CH | Cl | OCH₃ | OH | |
| 678 | H | O | CH | CH₃ | CH₃ | OC₃H₇ | |
| 679 | H | O | CH | CH₃ | CH₃ | OH | |
| 680 | H | O | CH | OCH₃ | OCH₃ | ON=C(CH₃)₂ | |
| 681 | H | O | CH | OCH₃ | OCH₃ | NHSO₂CH₃ | |
| 682 | H | O | CH | OCH₃ | OCH₃ | O—C₆H₅ | |

TABLE 53-continued

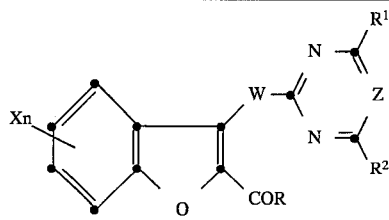

| Comp. No. | Xn | W | Z | R¹ | R² | R | Physical nature mp (°C.) $n_D^{20}$ |
|---|---|---|---|---|---|---|---|
| 683 | H | O | CH | OCH₃ | OCH₃ | 2-methylphenoxy | |
| 684 | H | O | CH | OCH₃ | OCH₃ | OCH₂-phenyl | |
| 685 | H | O | N | OCH₃ | OCH₃ | OCH₃ | |
| 686 | H | O | N | OCH₃ | OCH₃ | OH | |
| 687 | H | O | N | CH₃ | OCH₃ | OC₂H₅ | |
| 688 | H | O | N | CH₃ | OCH₃ | OH | |
| 689 | H | S | CH | OCH₃ | OCH₃ | OCH₃ | |

TABLE 54

| Comp. No. | Xn | W | Z | R¹ | R² | R | Physical nature mp (°C.) $n_D^{20}$ |
|---|---|---|---|---|---|---|---|
| 690 | H | S | CH | OCH₃ | OCH₃ | OH | |
| 691 | H | S | CH | Cl | OCH₃ | OCH₃ | |
| 692 | H | S | CH | Cl | OCH₃ | OH | |
| 693 | H | S | CH | OCHF₂ | OCH₃ | OCH₃ | |
| 694 | H | O | CH | OCHF₂ | OCH₃ | OH | |
| 695 | H | O | CH | OCHF₂ | OCHF₂ | OCH₃ | |
| 696 | H | O | CH | OCHF₂ | OCHF₂ | OH | |
| 697 | H | O | CH | OCHF₂ | OCH₃ | OCH₃ | |
| 698 | H | O | CH | OCHF₂ | OCH₃ | OH | |
| 699 | H | O | CH | N(CH₃)₂ | OCH₃ | OC₂H₅ | |
| 700 | H | O | CH | N(CH₃)₂ | OCH₃ | OH | |
| 701 | H | O | CH | SCH₃ | OCH₃ | OC₃H₇ | |
| 702 | H | O | CH | SCH₃ | OCH₃ | OH | |

TABLE 55

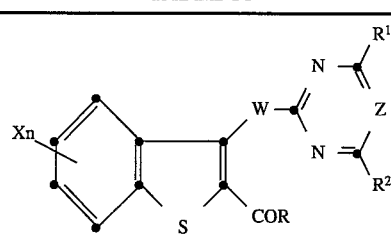

| Comp. No. | Xn | W | Z | R¹ | R² | R | Physical nature mp (°C.) $n_D^{20}$ |
|---|---|---|---|---|---|---|---|
| 703 | H | O | CH | OCH₃ | OCH₃ | OCH₃ | 133–136 |
| 704 | H | O | CH | OCH₃ | OCH₃ | OH | 143–146 |
| 705 | H | O | CH | Cl | OCH₃ | OC₂H₅ | |
| 706 | H | O | CH | Cl | OCH₃ | OH | |

TABLE 55-continued

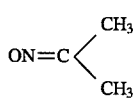

| Comp. No. | Xn | W | Z | R¹ | R² | R | Physical nature mp (°C.) $n_D^{20}$ |
|---|---|---|---|---|---|---|---|
| 707 | H | O | CH | CH₃ | CH₃ | OC₃H₇ | |
| 708 | H | O | CH | CH₃ | CH₃ | OH | |
| 709 | H | O | CH | OCH₃ | OCH₃ | ON=C(CH₃)(CH₃) | |
| 710 | H | O | CH | OCH₃ | OCH₃ | NHSO₂CH₃ | |
| 711 | H | O | CH | OCH₃ | OCH₃ | O-C₆H₅ | |
| 712 | H | O | CH | OCH₃ | OCH₃ | O-(2-CH₃-C₆H₄) | |
| 713 | H | O | CH | OCH₃ | OCH₃ | OCH₂-C₆H₅ | |
| 714 | H | O | N | OCH₃ | OCH₃ | OCH₃ | |
| 715 | H | O | N | OCH₃ | OCH₃ | OH | |
| 716 | H | O | N | CH₃ | OCH₃ | OC₂H₅ | |
| 717 | H | O | N | CH₃ | OCH₃ | OH | |

TABLE 56

| Comp. No. | Xn | W | Z | R¹ | R² | R | Physical nature mp (°C.) $n_D^{20}$ |
|---|---|---|---|---|---|---|---|
| 718 | H | S | CH | OCH₃ | OCH₃ | OCH₃ | |
| 719 | H | S | CH | OCH₃ | OCH₃ | OH | |
| 720 | H | S | CH | Cl | OCH₃ | OCH₃ | |
| 721 | H | S | CH | Cl | OCH₃ | OH | |
| 722 | H | S | CH | OCHF₂ | OCH₃ | OCH₃ | |
| 723 | H | S | CH | OCHF₂ | OCH₃ | OH | |
| 724 | H | O | CH | OCHF₂ | OCHF₂ | OCH₃ | |
| 725 | H | O | CH | OCHF₂ | OCHF₂ | OH | |
| 726 | H | O | CH | OCHF₂ | OCH₃ | OCH₃ | |
| 727 | H | O | CH | OCHF₂ | OCH₃ | OH | |
| 728 | H | O | CH | N(CH₃)₂ | OCH₃ | OC₂H₅ | |
| 729 | H | O | CH | N(CH₃)₂ | OCH₃ | OH | |
| 730 | H | O | CH | SCH₃ | OCH₃ | OCH₃ | |

TABLE 56-continued

| Comp. No. | Xn | W | Z | R¹ | R² | R | Physical nature mp (°C.) $n_D^{20}$ |
|---|---|---|---|---|---|---|---|
| 731 | H | O | CH | SCH₃ | OCH₃ | OH | |

TABLE 57

| Comp. No. | Xn | W | Z | R¹ | R² | R³ | R⁷ | Physical nature mp (°C.) $n_D^{20}$ |
|---|---|---|---|---|---|---|---|---|
| 732 | H | O | CH | OCH₃ | OCH₃ | CH₃ | OC₂H₅ | |
| 733 | H | O | CH | OCH₃ | OCH₃ | CH₃ | OH | |
| 734 | H | O | CH | Cl | OCH₃ | CH₃ | OCH₃ | |
| 735 | H | O | CH | Cl | OCH₃ | CH₃ | OH | |
| 736 | H | O | CH | N(CH₃)(CH₃) | OCH₃ | CH₃ | OC₂H₅ | |
| 737 | H | O | CH | N(CH₃)(CH₃) | OCH₃ | CH₃ | OH | |
| 738 | H | O | N | OCH₃ | OCH₃ | CH₃ | OC₃H₇ | |
| 739 | H | O | N | OCH₃ | OCH₃ | CH₃ | OH | |
| 740 | H | O | N | CH₃ | OCH₃ | CH₃ | OC₄H₉ | |
| 741 | H | O | N | CH₃ | OCH₃ | CH₃ | OH | |
| 742 | H | O | CH | SCH₃ | OCH₃ | CH₃ | OCH₃ | |
| 743 | H | O | CH | SCH₃ | OCH₃ | CH₃ | OH | |

TABLE 58

| Comp. No. | Xn | W | Z | R¹ | R² | R³ | R | Physical nature mp (°C.) $n_D^{20}$ |
|---|---|---|---|---|---|---|---|---|
| 744 | H | O | CH | OCH₃ | OCH₃ | H | OCH₃ | |
| 745 | H | O | CH | OCH₃ | OCH₃ | H | OH | |
| 746 | 7-F | O | CH | OCH₃ | OCH₃ | H | OCH₃ | |
| 747 | 7-F | O | CH | OCH₃ | OCH₃ | H | OH | |
| 748 | 7-N(CH₃)(CH₃) | O | CH | OCH₃ | OCH₃ | H | OCH₃ | |
| 749 | 7-N(CH₃)(CH₃) | O | CH | OCH₃ | OCH₃ | H | OH | |

TABLE 58-continued

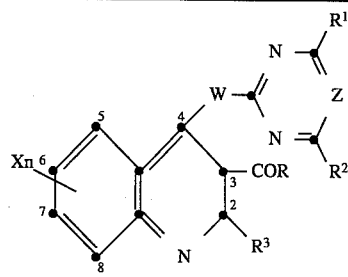

| Comp. No. | Xn | W | Z | R¹ | R² | R³ | R | Physical nature mp (°C.) $n_D^{20}$ |
|---|---|---|---|---|---|---|---|---|
| 750 | 7-CN | O | CH | OCH₃ | OCH₃ | H | OCH₃ | |
| 751 | 7-CN | O | CH | OCH₃ | OCH₃ | H | OH | |
| 752 | 7-NO₂ | O | CH | OCH₃ | OCH₃ | H | OCH₃ | |
| 753 | 7-NO₂ | O | CH | OCH₃ | OCH₃ | H | OH | |

TABLE 59

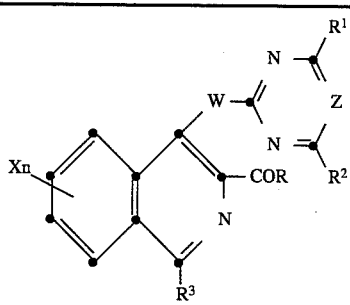

| Comp. No. | Xn | W | Z | R¹ | R² | R³ | R | Physical nature mp (°C.) $n_D^{20}$ |
|---|---|---|---|---|---|---|---|---|
| 754 | H | O | CH | OCH₃ | OCH₃ | Cl | OC₂H₅ | 1.5811 |
| 755 | H | O | CH | OCH₃ | OCH₃ | Cl | OH | |
| 756 | H | O | CH | OCH₃ | OCH₃ | H | OC₂H₅ | 93–96 |
| 757 | H | O | CH | OCH₃ | OCH₃ | H | OH | |
| 758 | H | O | CH | Cl | OCH₃ | Cl | OCH₃ | |
| 759 | H | O | CH | Cl | OCH₃ | Cl | OH | |
| 760 | H | O | CH | Cl | OCH₃ | H | OCH₃ | |
| 761 | H | O | CH | Cl | OCH₃ | H | OH | |

TABLE 60

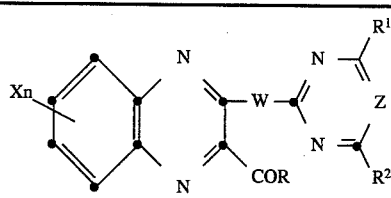

| Comp. No. | Xn | W | Z | R¹ | R² | R | Physical nature mp (°C.) $n_D^{20}$ |
|---|---|---|---|---|---|---|---|
| 762 | H | O | CH | OCH₃ | OCH₃ | OC₂H₅ | 1.5933 |
| 763 | H | O | CH | OCH₃ | OCH₃ | OH | |
| 764 | H | O | CH | Cl | OCH₃ | OC₂H₅ | |
| 765 | H | O | CH | Cl | OCH₃ | OH | |
| 766 | H | O | CH | OCHF₂ | OCH₃ | OCH₃ | |

TABLE 60-continued

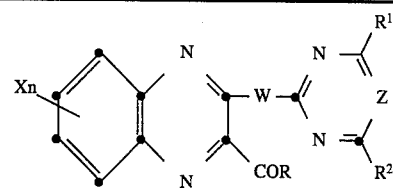

| Comp. No. | Xn | W | Z | R¹ | R² | R | Physical nature mp (°C.) $n_D^{20}$ |
|---|---|---|---|---|---|---|---|
| 767 | H | O | CH | OCHF₂ | OCH₃ | OH | |

The herbicide of the present invention comprises a pyrimidine or triazine derivative of the formula (I) as an active ingredient.

For the compound of the present invention to be used as a herbicide, the compound of the present invention may be used by itself. However, it may be used in the form of a formulation such as a dust, a wettable powder, an emulsifiable concentrate, a micro granule or a granule by blending it with a carrier which is commonly used for formulations, a surfactant, a dispersant or an adjuvant.

The carrier to be used for such formulations, may, for example, be a solid carrier such as Zeeklite, talc, bentonite, clay, kaolin, diatomaceous earth, fine silica, vermiculite, calcium carbonate, slaked lime, silica sand, ammonium sulfate or urea, or a liquid carrier such as isopropyl alcohol, xylene, cyclohexane or methylnaphthalene.

As the surfactant and dispersant, a metal salt of alkylbenzenesulfonic acid, a metal salt of dinaphthylmethane disulfonic acid, a salt of alcohol sulfuric acid ester, an alkylaryl sulfonate, a lignin sulfonate, a polyoxyethylene glycol ether, a polyoxyethylene alkylaryl ether or a polyoxyethylene sorbitol monoalkylate may, for example, be mentioned.

The adjuvant may, for example, be carboxymethyl cellulose, polyethylene glycol or gum arabic.

In practical use, the herbicide may be diluted to a suitable concentration before application, or may be directly applied.

The herbicide of the present invention may be used for application to foliage, soil or water surface. The blending proportion of the active ingredient is suitably selected as the case requires. However, in a case of a dust or a granule, the proportion of the active ingredient is selected suitably within a range of from 0.01 to 10% by weight, preferably from 0.05 to 5% by weight. In a case of an emulsifiable concentrate or a wettable powder, the proportion is selected suitably within a range of from 1 to 50% by weight, preferably from 5 to 20% by weight.

The dose of the herbicide of the present invention varies depending upon the type of the compound, the weeds to be controlled, the germination tendency, the environmental conditions and the type of the formulation to be used. However, in the case of a dust or a granule which is used by itself, the dose of the active ingredient is selected suitably within a range of from 0.1 g to 10 kg, preferably from 10 g to 5 kg, per 10 ares. In a case of an emulsifiable concentrate or a wettable powder which is used in a liquid state, the dose of the active ingredient is selected suitably within a range of from 0.1 to 100,000 ppm, preferably from 10 to 50,000 ppm.

Further, the compound of the present invention may be used in combination with an insecticide, a fungicide, other herbicide, a plant growth controlling agent, a fertilizer or the like, as the case requires.

Now, the formulation method will be described with reference to typical Formulation Examples. The compounds, types of the additives and blending ratios are not limited to such specific Examples and may be changed within wide ranges. In the following description, "parts" means "parts by weight".

FORMULATION EXAMPLE 1 (Wettable powder)

To 10 parts of Compound No. 625, 0.5 part of Emulgen (registered trade mark of Kao Corporation) 810, 0.5 part of Demol (registered trade mark of Kao Corporation) N, 20 parts of Kunilite (registered trade mark of Kunimine Kogyo K. K.) 201 and 69 parts of Zeeklite (registered trade mark of Zeeklite Co., Ltd) CA were mixed and pulverized to obtain a wettable powder.

FORMULATION EXAMPLE 2 (Wettable powder)

To 10 parts of Compound No. 675, 0.5 part of Emulgen 810, 0.5 part of Demol N, 20 parts of Kunilite 201, 5 parts of Carplex (registered trade mark of Shionogi & Co., Ltd.) 80 and 64 parts of Zeeklite CA were mixed and pulverized to obtain a wettable powder.

FORMULATION EXAMPLE 3 (Wettable powder)

To 10 parts of Compound No. 42, 0.5 part of Demol N, 0.5 part of Emal (registered trade mark of Kao Atlas K. K.) 10, 20 parts of Kunilite 301, 5 parts of Carplex 80 and 64 parts of calcium carbonate were mixed and pulverized to obtain a wettable powder.

FORMULATION EXAMPLE 4 (Emulsifiable concentrate)

To 10 parts of Compound No. 453, 80 parts of a mixture comprising equal amounts of xylene and isophorone and 10 parts of a surfactant Sorpol (registered trade mark of Toho Chemical Industries Co., Ltd.) 800A were added, and the mixture was thoroughly stirred to obtain an emulsifiable concentrate.

FORMULATION EXAMPLE 5 (Granule)

10 Parts of water was added to 1 part of Compound No. 13, 89 parts of a bulking agent comprising a 1:3 mixture of talc and bentonite, 5 parts of fine silica and 5 parts of a surfactant Sorpol 800A, and the mixture was thoroughly kneaded to obtain a paste, which was extruded through sieve apertures with a diameter of 0.7 mm. The extruded product was dried and then cut into a length of from 0.5 to 1 mm to obtain granules.

Now, the effects of the compounds of the present invention will be described with reference to Test Examples.

TEST EXAMPLE 1 (Test on herbicidal effects by paddy field soil treatment)

In a plastic pot (surface area: 100 $cm^2$) filled with paddy field soil, barnyardgrass (Ec), monochoria (Mo) and bulrush (Sc) were sown after puddling and leveling, and flooded to a water depth of 3 cm. Next day, a wettable powder prepared in accordance with Formulation Example 1 was diluted with water and applied dropwise to the water surface. The dose was 400 g of the active ingredient per ares. The plants were then cultured in a green house, and the evaluation of the herbicidal effects was conducted on the 21st day after the application in accordance with the standards as identified in Table 61. The results are shown in Table 62.

As a comparative agent, benzyl 3-(4,6-dimethoxypyrimidin-2-yl)oxy 2-naphthoate (disclosed in Japanese Unexamined Patent Publication No. 121973/1990: Compound No. 2.5) was used.

TABLE 61

| Index No. | Herbicidal effects (growth-controlling degree) |
|---|---|
| 5 | Herbicidal effect of control: at least 90% |
| 4 | Herbicidal effect: at least 70% and less than 90% |
| 3 | Herbicidal effect: at least 50% and less than 70% |
| 2 | Herbicidal effect: at least 30% and less than 50% |
| 1 | Herbicidal effect: at least 10 and less than 30% |
| 0 | Herbicidal effect: 0 to less than 10% |

TABLE 62

| Compound No. | Herbicidal effects | | |
|---|---|---|---|
| | Ec | Mo | Sc |
| 2 | 3 | 3 | 4 |
| 3 | 4 | 2 | 2 |
| 13 | 5 | 5 | 5 |
| 157 | 5 | 5 | 3 |
| 168 | 3 | 5 | 4 |
| 437 | 2 | 5 | 5 |
| 453 | 5 | 5 | 5 |
| 459 | 2 | 5 | 5 |
| 622 | 5 | 5 | 5 |
| 624 | 5 | 5 | 4 |
| 674 | 5 | 5 | 5 |
| 675 | 3 | 5 | 4 |
| Comparative agent | 1 | 2 | 1 |

TEST EXAMPLE 2 (Test on herbicidal effects by upland field soil treatment)

In a plastic pot (surface area: 120 cm²) filled with upland field soil, pale smartweed (Po), slender amaranth (Am), common lambsquarters (Ch) and rice flatsedge (Ci) were sown and covered with soil. A wettable powder prepared in accordance with Formulation Example 1 was diluted with water and applied uniformly to the soil surface by a small-sized sprayer in an amount of 100 l/10 ares so as to apply 400 g of the active ingredient per 10 ares. The plants were then cultured in a green house, and the evaluation of the herbicidal effects was conducted on the 21st day after the application in accordance with the standards as identified in Table 61. The results are shown in Table 63.

TABLE 63

| Compound No. | Herbicidal effects | | | |
| --- | --- | --- | --- | --- |
| | Po | Am | Ch | Ci |
| 13 | 3 | 4 | 2 | 5 |
| 22 | 5 | 3 | 5 | 3 |
| 24 | 5 | 5 | 3 | 4 |
| 27 | 5 | 4 | 2 | 2 |
| 153 | 5 | 2 | 5 | 3 |
| 157 | 4 | 5 | 5 | 4 |
| 168 | 5 | 5 | 4 | 2 |
| 453 | 5 | 5 | 5 | 5 |
| 624 | 3 | 5 | 5 | 4 |
| 625 | 4 | 5 | 5 | 4 |
| 674 | 2 | 5 | 5 | 3 |
| 675 | 3 | 5 | 4 | 5 |

TEST EXAMPLE 3 (Test on herbicidal effects by upland field foliage treatment)

In a plastic pot (surface area: 120 cm²) filled with upland field soil, pale smartweed (Po), slender amaranth (Am), common lambsquarters (Ch) and rice flatsedge (Ci) were sown and covered with soil and were cultured in a green house for 2 weeks. A wettable powder prepared in accordance with Formulation Example 1 was diluted with water and applied onto the entire foliages of the plants from above by a small-sized sprayer in an amount of 100 l/10 ares so as to apply 400 g of the active ingredient per 10 ares. The plants were then cultured in the green house, and the evaluation of the herbicidal effects was conducted on the 14th day after the treatment in accordance with the standards as identified in Table 61. The results are shown in Table 64.

TABLE 64

| Compound No. | Herbicidal effects | | | |
| --- | --- | --- | --- | --- |
| | Po | Am | Ch | Ci |
| 2 | 4 | 5 | 5 | 5 |
| 13 | 5 | 5 | 5 | 5 |
| 114 | 4 | 3 | 3 | 2 |
| 157 | 4 | 5 | 4 | 3 |
| 177 | 4 | 5 | 2 | 5 |
| 437 | 2 | 5 | 3 | 5 |
| 453 | 5 | 5 | 5 | 5 |
| 622 | 5 | 3 | 2 | 5 |
| 624 | 4 | 4 | 4 | 2 |
| 625 | 4 | 5 | 4 | 4 |
| 674 | 5 | 4 | 5 | 2 |
| 675 | 5 | 5 | 5 | 5 |

We claim:
1. A compound of the formula (I) or its salt:

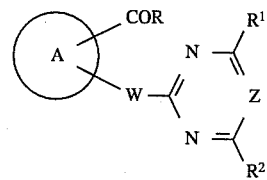

wherein A is a heterocyclic ring of the formula:

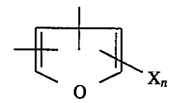

wherein

R is a hydrogen atom, a hydroxyl group, an imidazolyl group, a $C_1$–$C_6$ alkoxy group, a $C_3$–$C_6$ alkenyloxy group, a $C_3$–$C_6$ alkynyloxy group, a $C_1$–$C_6$ alkylthio group, a $C_3$–$C_7$ cycloalkoxy group, a benzyloxy group, a substituted benzyloxy group, a benzylthio group, a substituted benzylthio group, a $C_3$–$C_6$ cycloalkylthio group, a $C_1$–$C_4$ alkoxy $C_1$–$C_4$ alkoxy group, a furyloxy group, a tetrahydrofuryloxy group, a phenoxy group, a substituted phenoxy group, a $C_2$–$C_4$ aralkyloxy group, a $C_1$–$C_4$ alkylthio $C_1$–$C_4$ alkoxy group, a cyano $C_1$–$C_4$ alkoxy group, a $C_1$–$C_4$ alkoxycarbonyl $C_1$–$C_4$ alkoxy group, an N,N-di $C_1$–$C_3$ alkylamino $C_1$–$C_3$ alkoxy group, an N,N-di$C_1$–$C_3$ alkylamino $C_1$–$C_3$-alkylthio group, a $C_3$–$C_9$ linear or cyclic alkylidene aminoxy group, a $C_1$–$C_4$ alkylsufonylamino group, a phenylsulfonylamino group, a substituted phenylsulfonylamino group, a trimethylsilylethoxy group, a group of the formula —NR⁴R⁵ (wherein each of R⁴ and R⁵ which may be the same or different, is a hydrogen atom, a hydroxyl group, a $C_1$–$C_6$ alkyl group, a $C_1$–$C_6$ alkoxy group, a $C_3$–$C_6$ alkenyl group, a phenyl group, a substituted phenyl group, a $C_3$–$C_6$ cycloalkyl group, a $C_1$–$C_3$ alkoxy $C_1$–$C_3$ alkyl group, a $C_1$–$C_3$ acyl group, a $C_3$–$C_6$ alkynyl group, a $C_3$–$C_5$ alkenyloxy group, a $C_3$–$C_5$ alkynyloxy group, a benzyloxy group, a substituted benzyloxy group, a $C_1$–$C_4$ alkoxycarbonyl $C_1$–$C_3$ alkyl group, a $C_1$–$C_4$ alkoxycarbonyl $C_1$–$C_3$ alkoxy group, an amino group, a dimethylamino group, a cyano group, a $C_1$–$C_4$ alkylsulfonyl group, a phenylsulfonyl group, a substituted phenylsulfonyl group, an acetylamino group or an anilino group, or R⁴ and R⁵ may together form a ring which may contain an oxygen atom), each of R¹ and R² which may be the same or different, is a hydrogen atom (provided that a case where R¹ and R² are both hydrogen is excluded), a halogen atom, a $C_1$–$C_6$ alkyl group, a $C_1$–$C_6$ haloalkyl group, a $C_1$–$C_6$ alkoxy group, a $C_1$–$C_6$ haloalkoxy group, a $C_1$–$C_6$ alkylthio group, a phenoxy group, a substituted phenoxy group, a $C_1$–$C_3$ alkoxy $C_1$–$C_3$ alkyl group, a $C_3$–$C_6$ cycloalkyl group, a $C_2$–$C_5$ alkenyl group, a $C_3$–$C_5$ alkenyloxy group, a $C_2$–$C_4$ alkynyl group, a $C_3$–$C_5$ alkynyloxy group, a $C_1$–$C_3$ alkylthio $C_1$–$C_3$ alkyl group, a group of the formula —NR⁶R⁷ (wherein each of R⁶ and R⁷ which may be the same or different, is a hydrogen atom, a hydroxyl group, a $C_1$–$C_4$ alkyl group, a $C_1$–$C_4$ alkoxy group, a $C_2$–$C_4$ alkenyl group, a $C_3$–$C_5$ alkenyloxy group or a $C_3$–$C_5$ alkynyloxy group, or R⁶ and R⁷ may together form a ring which may contain an oxygen atom), X is a phenyl group, W is an oxygen atom, a sulfur atom or a group of the formula —NR¹⁰ (wherein R¹⁰ is a hydrogen atom, a $C_1$–$C_3$ alkyl group, a $C_2$–$C_5$ alkenyl group, a $C_2$–$C_4$ alkynyl group, a $C_1$–$C_3$ alkoxy $C_1$–$C_3$ alkyl group, a $C_1$–$C_3$ alkylsulfonyl group, a phenylsulfonyl group, a substituted phenylsulfonyl group, a $C_1$–$C_3$ acyl group, a benzoyl group or a substituted benzoyl group), Z is a methine group, and n is an integer of from 1 to 2.

2. A compound according to claim 1, wherein W is oxygen, $R^1$ and $R^2$ each are methoxy, R is OH and n is 1.

3. A herbicide containing a compound as defined in any one of claim 2, as a herbicidally active ingredient.

* * * * *

UNITED STATES PATENT AND TRADEMARK OFFICE
CERTIFICATE OF CORRECTION

PATENT NO. : 5,527,763
DATED : June 18, 1996
INVENTOR(S) : Masahiro MIYAZAKI, et al.

It is certified that error appears in the above-indentified patent and that said Letters Patent is hereby corrected as shown below:

On the title page, Item [75], the First through Fourth inventor's residence, should read:

-- [75] Iwata-gun. --

Signed and Sealed this

Seventeenth Day of September, 1996

Attest:

BRUCE LEHMAN

*Attesting Officer*   *Commissioner of Patents and Trademarks*